US006268146B1

(12) United States Patent
Shultz et al.

(10) Patent No.: US 6,268,146 B1
(45) Date of Patent: *Jul. 31, 2001

(54) ANALYTICAL METHODS AND MATERIALS FOR NUCLEIC ACID DETECTION

(75) Inventors: John William Shultz, Verona; Martin K. Lewis, Madison; Michelle Mandrekar, Oregon; Donna Leippe, Middleton; Roderick R. Smith, Jr., Fitchburg, all of WI (US); Roy Welch, Palo Alto, CA (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/425,460

(22) Filed: Nov. 22, 1999

Related U.S. Application Data

(63) Continuation-in-part of application No. 09/358,972, filed on Jul. 21, 1999, which is a continuation-in-part of application No. 09/252,436, filed on Feb. 18, 1999, which is a continuation-in-part of application No. 09/042,287, filed on Mar. 13, 1998.

(51) Int. Cl.[7] ............................. C12Q 1/68; C12P 19/34; G01N 24/00; C07H 19/04

(52) U.S. Cl. ............................. 435/6; 435/7; 435/91.2; 435/91.5; 436/173; 436/501; 536/26; 536/27; 536/28; 935/77; 935/82

(58) Field of Search ............................. 435/6, 91.2, 91.5, 435/7; 436/173, 501; 536/26, 27, 28; 935/77, 82

(56) References Cited

U.S. PATENT DOCUMENTS

| | | | |
|---|---|---|---|
| 4,303,752 | 12/1981 | Kolehmainen et al. | 435/8 |
| 4,331,762 | 5/1982 | Nakajima et al. | 435/190 |
| 4,338,395 | 7/1982 | Leon et al. | 435/17 |
| 4,352,881 | 10/1982 | Inagawa et al. | 435/17 |
| 4,357,420 | 11/1982 | Bostick et al. | 435/8 |
| 4,368,261 | 1/1983 | Klose et al. | 435/15 |
| 4,371,611 | 2/1983 | Fusee | 435/14 |
| 4,394,445 | 7/1983 | Nix et al. | 435/19 |
| 4,415,655 | 11/1983 | De Castro et al. | 435/17 |
| 4,438,124 | 3/1984 | Meister et al. | 424/270 |
| 4,443,594 | 4/1984 | Buckmann | 536/27 |
| 4,446,231 | 5/1984 | Self | 435/7 |
| 4,460,684 | 7/1984 | Bauer | 435/14 |
| 4,485,177 | 11/1984 | Siedel et al. | 436/547 |
| 4,595,655 | 6/1986 | Self | 435/7 |
| 4,683,195 | 7/1987 | Mullis et al. | 435/6 |
| 4,683,202 | 7/1987 | Mullis et al. | 435/91 |
| 4,735,897 * | 4/1988 | Vary et al. | 435/6 |
| 4,743,561 | 5/1988 | Shaffar | 436/501 |
| 4,755,458 | 7/1988 | Rabbani et al. | 435/5 |
| 4,800,159 | 1/1989 | Mullis et al. | 435/172.3 |
| 5,356,776 | 10/1994 | Kambara et al. | 435/6 |
| 5,389,512 | 2/1995 | Sninsky et al. | 435/5 |
| 5,391,480 | 2/1995 | Davis et al. | 435/6 |
| 5,399,491 | 3/1995 | Kacian et al. | 435/6 |

(List continued on next page.)

FOREIGN PATENT DOCUMENTS

| | | | |
|---|---|---|---|
| 0 229 601 | 11/1986 | (EP) . | |
| 639 647 | 7/1994 | (EP) . | |
| 0 663 447 | 12/1994 | (EP) . | |
| 0 894 867 | 11/1997 | (EP) . | |
| 2055200 | 12/1981 | (GB) | G01N/21/76 |
| WO 90/05530 | 5/1990 | (WO) . | |
| WO 91/17264 | 11/1991 | (WO) . | |
| WO 92/13963 | 8/1992 | (WO) . | |
| WO 94/25619 | 11/1994 | (WO) . | |
| WO 95/21938 | 8/1995 | (WO) . | |
| WO 96/41014 | 12/1996 | (WO) . | |
| WO 97/41256 | 11/1997 | (WO) . | |
| WO 98/13523 | 4/1998 | (WO) | C12Q/1/68 |
| WO 98/54362 | 4/1998 | (WO) . | |
| WO 98/28440 | 7/1998 | (WO) | C12Q/1/68 |

OTHER PUBLICATIONS

Seq ID No. 1, "Blast Archaeal Gemone Sequences at Center of Marine Biotechnology" Online, May 21, 1999, Retrieved on Aug. 7, 2000 @ http://Combdna.umbi.umd.edu/bags.html.

http://Comb5–156.umbi.umd.edu/cgi–bin/PfurGene.PL?GeneID=894645&Dataset=Nayb&Geneidtxt–994645, Online! XP002144446, Retrieved from the internet on Aug. 7, 2000.

Giartosio, et al., "Thermal stability of hexameric and tetrameric nucleoside diphosphate kinases: Effect of subunit interaction", *J. Biol. Chem.*, 271(30):17845–17851 (1996).

Bi, W., et al., "Detection of known mutation by proof–reading PCR", *Nucleic Acid Research*, GB, 26(12):3073–3075 (1998).

Kawarabayashi, et al., "Complete Sequence and Gene Organization of the Genorne of hyper–thermophilic Archaebacterium, *Pyrococcus horikoshii* OT3", *DNA Research*, 5:55–76 (1998).

A.E. Sippel, "Purification and Characterization of Adenosine Triphosphate: Ribonucleic Acid Adenyltransferase from *Escherichia coli*" *Eur. J. Biochem.* 37:31–40 (1973).

(List continued on next page.)

*Primary Examiner*—Jeffrey Fredman
*Assistant Examiner*—Arun Chakrabarti
(74) *Attorney, Agent, or Firm*—Welsh & Katz, Ltd.

(57) ABSTRACT

Mass spectrometric, absorbance spectroscopic and fluorescence spectroscopic processes are disclosed to detect the depolymerization of a nucleic acid hybrid in order to qualitatively and quantitatively assay for the presence of a predetermined nucleic acid target. Applications of those processes include the detection of single nucleotide polymorphisms, identification of single base changes, speciation, determination of viral load, genotyping, medical marker diagnostics, and the like, including multiplexed assays.

36 Claims, No Drawings

U.S. PATENT DOCUMENTS

| | | | |
|---|---|---|---|
| 5,403,711 | 4/1995 | Walder et al. | 435/6 |
| 5,445,933 | 8/1995 | Eadie et al. | 435/6 |
| 5,494,810 | 2/1996 | Barany et al. | 435/91.52 |
| 5,498,523 | 3/1996 | Tabor et al. | 435/6 |
| 5,512,439 | 4/1996 | Hornes et al. | 435/6 |
| 5,516,663 | 5/1996 | Backman et al. | 435/91.2 |
| 5,530,192 | 6/1996 | Murase et al. | 800/205 |
| 5,541,311 | 7/1996 | Dahlberg et al. | 536/23.7 |
| 5,561,044 | 10/1996 | Walker et al. | 435/6 |
| 5,573,906 | 11/1996 | Bannwarth et al. | 435/6 |
| 5,622,824 | 4/1997 | Koster et al. | 435/6 |
| 5,648,232 | 7/1997 | Squirrell | 435/34 |
| 5,660,988 | 8/1997 | Duck et al. | 435/6 |
| 5,667,964 | 9/1997 | Ho | 435/5 |
| 5,683,877 | 11/1997 | Lu-Chang et al. | 435/6 |
| 5,691,146 | 11/1997 | Mayrand | 435/6 |
| 5,723,591 | 3/1998 | Livak et al. | 536/22.1 |
| 5,731,146 | 3/1998 | Duck et al. | 435/6 |
| 5,736,365 | 4/1998 | Walker et al. | 435/91.2 |
| 5,741,635 | 4/1998 | Boss et al. | 435/4 |
| 5,759,820 | 6/1998 | Hornes et al. | 435/91.1 |
| 5,763,181 | 6/1998 | Han et al. | 435/6 |
| 5,766,849 | 6/1998 | McDonough et al. | 435/6 |
| 5,786,139 | 7/1998 | Burke et al. | 435/6 |
| 5,786,183 | 7/1998 | Ryder et al. | 435/91.2 |
| 5,814,491 | 9/1998 | Vijg et al. | 435/91.2 |
| 5,824,517 | 10/1998 | Cleuziat et al. | 435/91.2 |
| 5,834,202 | 10/1998 | Auerbach | 435/6 |
| 5,840,873 | 11/1998 | Nelson et al. | 536/24.3 |
| 5,843,660 | 12/1998 | Schumm et al. | 435/6 |
| 5,849,547 | 12/1998 | Cleuziat et al. | 435/91.21 |
| 5,853,981 | 12/1998 | Kondo et al. | 435/5 |
| 5,854,033 | 12/1998 | Lizardi | 435/91.2 |
| 5,861,242 | 1/1999 | Chee et al. | 435/5 |
| 5,863,736 | 1/1999 | Haaland | 435/6 |
| 5,866,337 | 2/1999 | Schon | 435/6 |
| 5,869,252 | 2/1999 | Bouma et al. | 435/6 |
| 5,871,902 | 2/1999 | Weininger et al. | 435/5 |
| 5,876,924 | 3/1999 | Zhang et al. | 435/5 |
| 5,876,930 | 2/1999 | Livak et al. | 435/6 |
| 5,876,978 | 3/1999 | Willey et al. | 435/91.2 |
| 5,880,473 | 3/1999 | Ginestet | 250/458.1 |
| 5,882,856 | 3/1999 | Shuber | 435/6 |
| 5,885,775 | 3/1999 | Haff et al. | 435/6 |
| 5,888,819 | 3/1999 | Goelet et al. | 435/5 |
| 5,902,722 | 5/1999 | Di Cesare et al. | 435/4 |
| 6,007,987 | 12/1999 | Cantor et al. | 435/6 |
| 6,066,483 | 5/2000 | Riggs et al. | 435/194 |

OTHER PUBLICATIONS

K.Chowdhury, N. Kaushik, V.N. Pandey and M.J. Modak, "Elucidiation of the Role of Arg 110 of Murine Leukemia Virus Reverse Transcriptase in the Catalytic Mechanism: Biochemical Characterization of Its Mutant Enzymes," *Biochemistry*, 35:16610–16620 (1996).

S. Karamohamed, M. Ronaghi and P. Nyren, "Bioluminometric Method for Real–Time Detection of Reverse Transcriptase Activity", *Biotechniques*, 24:302–306 (Feb., 1998).

B. Hove–Jensen, K.W. Harlow, C.J. King, R.L. Switzer, "Phosphoribosylpyrophosphate Synthetase of *Escherichia coli*", *J. Biol. Chem.*, 261(15):6765–6771 (1986).

P. Nyren, S. Karamohamed and M. Ronaghi, "Detection of Single–Base Changes Using a Bioluminometric Primer Extension Assay", *Anal. Biochem.*, 244:367–373 (Jan. 15, 1997).

M. Ronaghi, S. Karamohamed, B. Pettersson, M. Uhlen and P. Nyren, "Real–Time DNA Sequencing Using Detection of Pyrophosphate Release," *Anal. Biochem.*, 242:84–89 (1996).

T.A. Rozovskaya, V.O. Rechinsky, R.S. Bibilashvili, M.Y. Karpeisky, N.B. Tarusova, R.M. Khomutov, H.B.F. Dixon, "The Mechanism of Pyrophosphorolysis of RNA by RNA Polymerase", *Biochem. J.*, 224: 645–650 (1989).

M.P. Deutscher and A. Kornberg, "Enzymatic Synthesis of Deoxyribonucleic Acid", *J. Biol. Chem.*, 244(11):3019–28 (1969).

J.D. Moyer and J.F. Henderson, "Nucleoside Triphosphate Specificity of Firefly Luciferase", *Anal. Biochem.*, 131:187–189 (1983).

C. Blondin, L. Serina, L. Weismuller, A. Gilles and O. Barzu, "Improved Spectrophotometric Assay of Nucleoside Monophosphate Kinase Activity Using the Pyruvate Kinase/Lactate Dehydrogenase Coupling System", *Anal. Biochem.*, 220:219–21 (1994).

S. Tabor and C.C. Richardson, "DNA Sequence Analysis With a Modified Bacteriophage T7 DNA Polymerase", *J. Biol. Chem.*, 265(14):8322–8328 (1990).

R.S. Chittock, J.–M. Hawronsky, J. Holah and C.W. Wharton, "Kinetic Aspects of ATP Amplification Reactions", *Anal. Biochem.*, 255:120–126 (Jan. 1, 1998).

Kung, et al., "Picogram Quantitation ofTotal DNA Using DNA–Binding Proteins in a Silicon Sensor–Based System", *Anal. Biochem.*, 187:220–227 (1990).

Srivastavan & Modak, *J. Biol. Chem.*, 255(5):2000–2004 (1980).

Sano & Feix, *Eur. J. Biochem.*, 71:577–583 (1976).

Sabina, et al., *Science*, 223:1193–1195 (1984).

Parks & Agarwal in *The Enzymes*, vol. 9:307–333, P. Boyer Ed. (1973).

Shimofuruya & Suzuki, *Biochem. Intl.*, 26(5):853–861 (1992).

Nyren, et al., "Detection of Single–Base Changes Using a Bioluminometric Primer Extension Assay", *Anal. Biochem.*, 244:367–373 (1997).

P. Bernard et al., *Am. J. Pathol.*, 153:1055–1061 (1998).

G. Garinis et al., *J. Clin. Lab. Anal.*, 13:122–125 (1999).

Holguin, et al., *Eur. J. Clin. Microbiol. Infect. Dis.*, 18:256–259 (1999).

Boriskin, et al., *Arch. Dis. Child.*, 80:132–136 (1999).

de Vega, et al., "Primer Terminus Stabilizing at the 3'–5' exonuclease active site of _29 DNA polymerase. Involvement of two amino acid residues highly conserved in proof-reading DNA polymerases", *EMBO J.*, 15(5):1182–1192 (1996).

S. Patel et al., *Biochemistry*, 30:511–525 (1991).

I. Wong et al., *Biochemistry*, 30:526–537 (1991).

S. Zinnen et al., *J. Biological Chemistry*, 269(39):24195–24202 (1994).

J. Lindquist, Dept. of Bacteriology, University of Wisconsin–Madison,http://www.bact.wisc.edu/bact102/102dil3.html undated.

J. Lindquist, Dept. of Bacteriology, University of Wisconsin–Madison, http://www.bact.wisc.edu/bact102/102dil3a.html undated.

Most Probable Number (MPN), WQA Glossary of Terms, 3rd Ed., Water Quality Association undated.

P. Nyren, B. Pettersson, and M. Uhlen. "Solid Phase DNA Minisequencing by an Enzymatic Luminometric Inorganic Pyrophosphate Detection Assay,"*Anal. Biochem.*, 208:171–175 (1993).

M. Ronaghi, S. Karamohamed, B. Pettersson, M. Uhlen, and P. Nyren, "Real–Time DNA Sequencing Using Detection of Pyrophosphate Release," *Anal. Biochem.*, 242:84–89 (1996).

J. Shultz, D. Leippe, K. Lewis, R. Lyke, M. Nelson, and C. Reynolds., "Detection of Low Levels of Nucleic Acids by Enzymatic Conversion to Substrates for Luciferase", Poster presented Jul. 25–29, 1998 at a Protein Society meeting in San Diego, California.

Heid, et al., "Real Time Quantitative PCR", *Genome Research*, 6:986–994 (1996).

Nagano, et al., "Detection of Verotoxin–Producing *Escherichia coli* O157:H7 by Multiplex Polymerase Chain Reaction", *Microbiol. Immunol.*, 42(5), 372–376 (1998).

Sherlock, et al., "Assessment of diagnostic quantitative fluorescent multiplex polymerase chain reaction assays performed on single cells", *Ann. Hum. Genet.* 62:9–23 (1998).

Axton, et al., "A Single–Tube Multiplex System for the Simultaneous Detection of 10Common Cystic Fibrosis Mutations", *Human Mutation*, 5:260–262 (1995).

Poyser et al., "Multiplex genotyping for cystic fibrosis from filter paper blood spots", *Ann. Clin. Biochem.*, 35:611–615 (1998).

Caudai, et al., "Detection of HCV and GBV–C/HGV injection by multiplex PCR in plasma samples of transfused subjects", *J. Virol Meth.*, 70:79–83 (1998).

Songsivilai, et al., "Improved Amplification System for Detection of Hepatitis C virus Genome that Simultaneously Differentiates Viral Genotype", *Southeast Asian J. Trop. Med. Public Health*, 27(2): 237–243 (1996).

Oyofo, et al., "Detection of Enterotoxigenic *Escherichia coli*, Shigella and Campylobacter spp. by Multiplex PCR Assay", *J. Diarrhoeal Dis. Res.*, 14(3): 207–210 (1996).

L. Ripoll, et al., "Multiplex PCR–mediated Site–directed Mutagenesis for One–step Determination of Factor V Leiden and G20210A Transition of the Prothrombin Gene", pp. 960–961 (1997).

L. Ripoll, et al., "Multiplex ASA PCR for a Simultaneous Determination of Factor V Leiden Gene, G—A 20210 Prothrombin Gene and C—T 677 MTHFR Gene Mutations", *Thromb Haemost*, 79:1054–1055 (1998).

X. Xu et al., "Two Multiplex PCR–Based DNA Assays for the Thrombosis Risk Factors Prothrombin G20210A and Coagulation Factor V G1691A Polymorphisms", *Thrombosis Research* 93:265–269 (1999).

E. Gomez, et al., "Rapid Simultaneous Screening of Factor V Leiden and G20210A Prothrombin Variant by Multiplex Polymerase Chain Reaction on Whole Blood", *Blood* 91(6): 2208–2211 (1998).

D. Linfert, et al., "Rapid Multiplex Analysis for the Factor V Leiden and Prothrombin G20210A Mutations Associated with Hereditary Thrombophilia", *Connecticut Medicine* 62(9):519–525 (1998).

P. Nyren, et al., *Anal. Biochem.*, 244:367–373 (1997).

S. Borman, "Developers of Novel DNA Sequencers Claim Major Performance Advances", *C&EN*, pp. 37–40 (Jul. 24, 1995).

P. Belgrader, et al., "PCR Detection of Bacteria in Seven Minutes", *Science Magazine* 284:449–450 (1999).

K. Hayashi *Genetic Analysis: Techniques and Applications* 9:73–79 (1992).

Newton et al., *Nucl. Acids Res.*, 17:2503–2516 (1989).

Wu et al., *Proc. Natl. Acad. Sci.*, USA, 86:2757–2760 (1989).

T. Nikiforov, et al., *Nucl. Acids Res.*, 22:4167–4175 (1994).

C. Wittwer, et al., *Biotechniques*, 22:130–138 (1997).

P. Holland, et al., *Proc. Natl. Acad. Sci.*, USA, 88:7276–7280 (1991).

R. Kramer, et al., *Nat. Biotechnol.*, 14:303–308 (1996).

J. Shultz, D. Leippe, K. Lewis and M. Nelsen, "Non–radioactive Measurement of DNA Using Coupled Enzymatic Reactions", Presentation Mar. 16–20, 1998 at a Parenteral Drug Association meeting in San Francisco, California.

\* cited by examiner

SEQUENCE LISTING

<160> NUMBER OF SEQ ID NOS: 10

<210> SEQ ID NO 1
<211> LENGTH: 74
<212> TYPE: DNA
<213> ORGANISM: Cytomegalovirus

<400> SEQUENCE: 1
ccaacagacg ctccacgttc tttctgacgt attcgtgcag catggtctgc gagcattcgt    60
ggtagaagcg agct                                                      74

<210> SEQ ID NO 2
<211> LENGTH: 21
<212> TYPE: DNA
<213> ORGANISM: Cytomegalovirus

<400> SEQUENCE: 2
ctaccacgaa tgctcgcaga c                                              21

<210> SEQ ID NO 3
<211> LENGTH: 21
<212> TYPE: DNA
<213> ORGANISM: Cytomegalovirus

<400> SEQUENCE: 3
ctaccacgaa tgctcgcaga t                                      21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:probe to
      prothrombin pcr product, with phosphorothiate linkage between the
      first five  bases on the 5' end

<400> SEQUENCE: 4
atagcactgg gagcattgag gc                                     22

<210> SEQ ID NO 5
<211> LENGTH: 20
<212> TYPE: DNA
<213> ORGANISM: Homo sapiens

<400> SEQUENCE: 5
gcacagacgg ctgttctctt                                        20

<210> SEQ ID NO 6
<211> LENGTH: 13
<212> TYPE: DNA
<213> ORGANISM: Homo sapiens

<400> SEQUENCE: 6
gtgattctca gca                                               13

<210> SEQ ID NO 7
<211> LENGTH: 13
<212> TYPE: DNA
<213> ORGANISM: Homo sapiens

<400> SEQUENCE: 7
gtgattctca gcg                                               13

<210> SEQ ID NO 8
<211> LENGTH: 22
<212> TYPE: DNA
<213> ORGANISM: Homo sapiens

<400> SEQUENCE: 8
tgcccagtgc ttaacaagac ca                                     22

<210> SEQ ID NO 9
<211> LENGTH: 20
<212> TYPE: DNA
<213> ORGANISM: Homo sapiens

<400> SEQUENCE: 9
tgttatcaca ctggtgctaa                                        20

<210> SEQ ID NO 10
<211> LENGTH: 22
<212> TYPE: DNA
<213> ORGANISM: Homo sapiens -continued

```
<400> SEQUENCE: 10
gacaaaatac ctgtattcct tg                                              22
```

ANALYTICAL METHODS AND MATERIALS FOR NUCLEIC ACID DETECTION

CROSS-REFERENCE TO RELATED APPLICATIONS

This application is a continuation-in-part of U.S. Ser. No. 09/358,972, filed on Jul. 21, 1999, which is a continuation-in-part of U.S. Ser. No. 09/252,436, filed on Feb. 18, 1999, which is a continuation-in-part of U.S. Ser. No. 09/042,287, filed Mar. 13, 1998, all of which are incorporated herein by reference.

TECHNICAL FIELD

The invention relates to nucleic acid detection. More specifically, the invention relates to the analytical methods for the detection of targeted, predetermined nucleic acid sequences in nucleic acid target/probe hybrids, and various applications of their detection.

BACKGROUND OF THE INVENTION

Methods to detect nucleic acids and to detect specific nucleic acids provide a foundation upon which the large and rapidly growing field of molecular biology is built. There is constant need for alternative methods and products. The reasons for selecting one method over another are varied, and include a desire to avoid radioactive materials, the lack of a license to use a technique, the cost or availability of reagents or equipment, the desire to minimize the time spent or the number of steps, the accuracy or sensitivity for a certain application, the ease of analysis, or the ability to automate the process.

The detection of nucleic acids or specific nucleic acids is often a portion of a process rather than an end in itself. There are many applications of the detection of nucleic acids in the art, and new applications are always being developed. The ability to detect and quantify nucleic acids is useful in detecting microorganisms, viruses and biological molecules, and thus affects many fields, including human and veterinary medicine, food processing and environmental testing. Additionally, the detection and/or quantification of specific biomolecules from biological samples (e.g. tissue, sputum, urine, blood, semen, saliva) has applications in forensic science, such as the identification and exclusion of criminal suspects and paternity testing as well as in genetics and medical diagnostics.

Some general methods to detect nucleic acids are not dependent upon a priori knowledge of the nucleic acid sequence. A luminescent nucleic acid detection method described in U.S. Pat. No. 4,735,897 is not sequence specific, indicates the presence of single-stranded RNA, such as mRNA. In the disclosed method, RNA is depolymerized using a polynucleotide phosphorylase (PNP) in the presence of phosphate or using a ribonuclease. That patent teaches that PNP stops depolymerizing when a double-stranded RNA segment is encountered, such as in single-stranded RNA with secondary structure, as is common in ribosomal RNA, transfer RNA, viral RNA, and the message portion of mRNA. PNP depolymerization of the polyadenylated tail of mRNA in the presence of inorganic phosphate forms ADP. Alternatively, depolymerization of RNA using a ribonuclease releases AMP. The released AMP is converted to ADP with myokinase, and ADP is converted into ATP by pyruvate kinase or creatine phosphokinase. Either the ATP or the byproduct from the organophosphate co-reactant (pyruvate or creatine) is detected as an indirect method of detecting mRNA. In U.S. Pat. No. 4,735,897, ATP is detected by a luminescence spectroscopic luciferase detection system. In the presence of ATP and oxygen, luciferase catalyzes the oxidation of luciferin, producing light that can then be quantified using a luminometer. Additional products of the reaction are AMP, pyrophosphate and oxyluciferin.

Hybridization methods to detect nucleic acids are dependent upon knowledge of the nucleic acid sequence. Many known nucleic acid detection techniques depend upon specific nucleic acid hybridization in which an oligonucleotide probe is hybridized or annealed to nucleic acid in the sample or on a blot, and the hybridized probes are detected.

Several hybridization methods to detect nucleic acids are discussed in the paragraphs that follow. These include PCR, Southern blots, and fluorescent hybridization with and without PCR. Several of hybridization methods are even useful for detecting specific nucleic acid sequences such as single nucleotide polymorphisms (SNPs), and distinguishing them from very similar sequences, and this is also discussed.

Polymerase chain reaction (PCR) and Southern blot-based hybridization methods for the detection of predetermined nucleic acid rely upon the use of hybridizing labeled primers or probes. Such probes have been labeled and detected using radioactivity; fluorescent spectroscopic methods using fluorescent dyes, acridinium esters and digoxygenin; and absorbance spectroscopic (often visible) methods using horseradish peroxidase, jack bean urease and alkaline phosphatase. PCR products made with unlabeled primers may be detected in other ways, such as electrophoretic gel separation followed by dye-based visualization.

There are hybridization assays to detect nucleic acid that involve fluorescence spectroscopic techniques utilizing energy transfer effects between fluorophores (FRET). U.S. Pat. No. 5,691,146 describes the use of fluorescent hybridization probes that are fluorescence-quenched unless they are hybridized to the target nucleic acid sequence. U.S. Pat. No. 5,723,591 describes fluorescent hybridization probes that are fluorescence-quenched until hybridized to the target nucleic acid sequence, or until the probe is digested. Such techniques provide information about hybridization, and are of varying degrees of usefulness for the determination of single base variances in sequences. Some fluorescence techniques involve digestion of the probe in a nucleic acid hybrid in a 5' to 3' direction to release a fluorophore providing a signal from proximity with a fluorescence quencher, thereby increasing the signal, for example, U.S. Pat. Nos. 5,691,146 and 5,876,930.

The fluorescence spectroscopic techniques for detection of nucleic acid hybrids have been applied to real-time (or kinetic) PCR and single nucleotide polymorphism (SNP) detection. Many of these systems are platform based and require specialized equipment, complicated primer design and expensive supporting materials for SNP detection. SNP detection using real-time PCR amplification relies on the ability to detect amplified segments of nucleic acid as they are made during the amplification reaction. Three basic real-time SNP detection methodologies exist: (i) increased fluorescence of double-stranded DNA-specific dye binding, (ii) decreased quenching of fluorescence during amplification (e.g. Taqman®), and (iii) increased fluorescence energy transfer during amplification (C. Wittwer et al., *Biotechniques*, 22:130–138 (1997)). All of these techniques are non-gel based and each strategy is briefly discussed below.

A variety of dyes are known to exhibit increased fluorescence in response to binding double stranded DNA. Production of wild type or mutation containing-PCR products are continuously monitored by the increased fluorescence of dyes such as ethidium bromide or syber green as they bind to the accumulating duplex PCR product. Note that dye binding is not selective for the sequence of the PCR product, and elevated levels of non-specific background can give rise to false signals with this technique.

Some technologies for real time detection of PCR products are based on detecting nucleic acid hybrids using fluorescence resonance energy transfer (FRET; mentioned above). These technologies either indirectly measure the amplification reaction through the use of a separate, labeled probe that hybridizes with but is not incorporated into the amplification product (U.S. Pat. Nos. 5,348,853; 5,119,801; 5,312,728; 5,962,233; 5,945,283; 5,876,930; 5,723,591; and 5,691,146) or directly detect amplification products through the use of a label directly incorporated in the amplification primer(s) (U.S. Pat. No. 5,866,336).

One such FRET-based technology for real time PCR product detection is known generally as 5' nuclease PCR assay (TaqMan® assay). In this assay the decrease in fluorescence quenching resulting from the cleavage of dually-labeled probes that hybridize downstream of amplification primers is monitored in an amplification reaction. A polymerase extends the growing nucleic acid chain from the amplification primers, and degrades hybridized dually-labeled probes from their 5'-termini using the 5' to 3' exonuclease activity of thermostable polymerases such as Taq DNA Polymerase. C. Wittwer et al., *Biotechniques*, 22:130–138 (1997); P. Holland et al, *Proc. Natl. Acad. Sci., USA*, 88:7276–7280 (1991). Although complementary to the PCR product, the fluorescently-labeled nucleic acid hybrid-detecting probes used in this assay are distinct from the PCR primers. The probes are dually-labeled with both a molecule capable of fluorescence and a molecule capable of quenching fluorescence. When the probes are intact, and hybridize to an amplification template, intramolecular quenching of energy between the two fluorophores (dual labels) of the probe leads to low, background levels of fluorescent signal. When a fluorescent molecule is liberated from the proximity of the fluorescence quencher by the exonuclease activity of a DNA polymerase (e.g. Taq DNA Polymerase) during amplification, the quenching is greatly reduced leading to increased fluorescent signal. This probe is degraded by the 5'-exonuclease activity of DNA polymerase when it hybridizes downstream of polymerase on the segment of DNA template being amplified.

In the TaqMan® assay, the donor and quencher are preferably located on the 3' and 5'-ends of the probe respectively, because the requirement that 5' to 3' hydrolysis be performed between the fluorophore and the quencher is met only when these two moieties are not too close to each other. Lyamichev et al., *Science*, 260:778–783, (1993). However, this can be a drawback of the assay since efficiency of energy transfer decreases with the inverse sixth power of the distance between the reporter and quencher. As a result, the background emissions from unhybridized probe can be high since the assay does not permit the quencher to be close enough to the reporter to achieve the most efficient quenching. In addition, not all of the probe hybridized to the PCR product will be hydrolyzed, some will be displaced without hydrolysis resulting in a loss of signal.

An additional form of real-time PCR product detection, termed molecular beacon assay, also capitalizes on the intramolecular quenching of a fluorescent molecule by use of a tethered quenching moiety. The molecular beacon technology utilizes hairpin-shaped, hybridization probe molecules with an internally-quenched fluorophore whose fluorescence is restored by binding to a DNA target of interest (Tyagi and Kramer, *Nat. Biotechnol.*, 14:303–308 (1996), U.S. Pat. Nos. 5,119,801 and 5,312,728). When used in PCR reactions, the molecular beacon probe, which hybridizes to one of the strands of the PCR product emits fluorescence, while those that remain unhybridized are fluorescence-quenched. As a result, the amount of fluorescence will increase as the amount of PCR product increases. Increased binding of the molecular beacon probe to the accumulating PCR product can be used to specifically detect SNPs present in genomic DNA.

However, it is unlikely that the beacon probes will hybridize quantitatively to one strand of double-stranded PCR product, especially when the amplification product is much longer than the beacon probe. Even those probes that are hybridized could be displaced by the second DNA strand over a short period of time; as a result, this method cannot be quantitative.

U.S. Pat. No. 5,885,775 discloses a hybridization method to determine the presence of nucleic acids utilizing mass spectrometric analysis. The method disclosed therein for determining sequence information, including SNPs, involves hybridizing one or more oligonucleotide probes having a nucleotide sequence complementary to a portion of the sample polynucleotide to form a complex. The formed complex is then contacted with at least a member selected from the group consisting of nucleosides, dideoxynucleosides, polymerase, nucleases, transcriptases, ligases and restriction enzymes to alter at least of a subset of the oligonucleotide probes. Then the molecular weight of the altered probes is determined using mass spectrometry, and the sequence of the sample polynucleotide is inferred.

A method disclosed in U.S. Pat. No. 5,885,775 for SNP determination involves the use of an extension primer hybridized such that the 3'-terminus of the primer is at the putative point mutation, and after reacting with polymerase and nucleotides the identity of the added nucleotide in the extension product is determined using mass spectrometry. A multiplex format is also disclosed for this polymerase extension assay.

Another method disclosed in U.S. Pat. No. 5,885,775 for SNP determination involves the use of a ligase or a ligase extension, wherein two hybridized primers are linked at a putative point mutation site. A multiplex format is also disclosed.

Another method disclosed in U.S. Pat. No. 5,885,775 is a "combinatorial" chain termination sequencing method wherein primers are extended in the presence of some ddNTPs to produce a ladder. Alternatively, a ladder of different length polynucleotides is produced by treating the extension products with an exonuclease activity from one of the following enzymes: phosphodiesterase type I, exonuclease I, exonuclease III, exonuclease V, exonuclease VII, and DNA polymerase III. A multiplex format is also disclosed.

Enzymes having template-dependent polymerase activity for which some 3' to 5' depolymerization activity has been reported include *E. coli* DNA Polymerase (Deutscher and Kornberg, *J. Biol. Chem.*, 244(11):3019–28 (1969)), T7 DNA Polymerase (Wong et al., *Biochemistry*, 30:526–37 (1991); Tabor and Richardson,*J. Biol. Chem.*, 265: 8322–28 (1990)), *E. coli* RNA polymerase (Rozovskaya et al., *Biochem. J.*, 224:645–50 (1994)), AMV and RLV reverse transcriptases (Srivastava and Modak, *J. Biol. Chem.*, 255: 2000–4 (1980)), and HIV reverse transcriptase (Zinnen et al., *J. Biol. Chem.*, 269:24195–202 (1994)). A template-dependent polymerase for which 3' to 5' exonuclease activity has been reported on a mismatched end of a DNA hybrid is phage 29 DNA polymerase (de Vega, M. et al. *EMBO J.*, 15:1182–1192, 1996).

There is a need for alternative methods for the detection of nucleic acid hybrids. There is a demand for highly sensitive methods that are useful for determining the presence or absence of specific nucleic acid sequences, for example methods to determine viral load that are able to reliably detect as few as 10 copies of a virus present in a body, tissue, fluid, or other biological sample. There is a great demand for methods to determine the presence or absence of nucleic acid sequences that differ slightly from sequences that might otherwise be present. There is a great demand for highly specific methods to determine the presence or absence of sequences unique to a particular species in a sample. There is also a great demand for such methods that are rapid and more sensitive than the known methods, highly reproducible and automatable with a flexible format.

It would be beneficial if another method were available for detecting the presence of a sought-after, predetermined target nucleotide sequence or allelic variants. It would also be beneficial if such a method were operable using a sample size of the microgram to picogram scale. It would further be beneficial if such a detection method were capable of providing multiple analyses in a single assay (multiplex assays).

In contrast to the techniques discussed before, a process of this invention discussed hereinafter has been designed as a modular technology that can use a variety of instruments that are suited to the throughput needs of the end-user and have a flexible and open system architecture for detection analysis. Alternative analytical detection methods, such as mass spectrometry, absorbance and fluorescence spectroscopic detection methods are used in a process of this invention, providing additional assay flexibility. The disclosure that follows thus provides a method that provides alternatives to the existing nucleic acid hybrid detection systems.

BRIEF SUMMARY OF THE INVENTION

A method of this invention is used to determine the presence or absence of a predetermined (known) nucleic acid target sequence in a nucleic acid sample. Such a method utilizes an enzyme that depolymerizes the 3'-terminus of an oligonucleotide probe hybridized to a nucleic acid target sequence to release one or more identifier nucleotides whose presence can then be determined.

One embodiment of the invention contemplates a method for determining the presence or absence of a predetermined nucleic acid target sequence in a nucleic acid sample. Thus, the presence or absence of at least one predetermined nucleic acid target sequence is sought to be determined. The presence or absence of more than one predetermined target sequence is determined in a single sample being assayed using methods of the invention. An embodiment comprises the following steps.

A treated sample is provided that may contain a predetermined nucleic acid target sequence hybridized with a nucleic acid probe that includes an identifier nucleotide in the 3'-terminal region. The treated sample is admixed with a depolymerizing amount of an enzyme whose activity is to release one or more nucleotides from the 3'-terminus of a hybridized nucleic acid probe to form a treated reaction mixture. The treated reaction mixture is maintained under depolymerizing conditions for a time period sufficient to permit the enzyme to depolymerize hybridized nucleic acid and release identifier nucleotides therefrom. The presence of released identifier nucleotides is analyzed to obtain an analytical output, the analytical output indicating the presence or absence of the nucleic acid target sequence. The analytical output is obtained by mass spectrometry, fluorescence spectroscopy or absorption spectroscopy as discussed herein.

In one embodiment, the analytical output is obtained by fluorescence spectroscopy. Use of a wide variety of fluorescence detection methods is contemplated. In one exemplary contemplated method, an identifier nucleotide includes a fluorescent label. An identifier nucleotide is fluorescently labeled prior to, or after, release of the identifier nucleotide. It is also contemplated that other than a released nucleotide contains a label such as a fluorescent tag. When a label is on other than a released nucleotide, the release of nucleotide is ascertained by monitoring the change in length of the labeled remainder of the depolymerized probe, or by a change in fluorescence when the identifier nucleotide includes a molecule capable of quenching or enhancing fluorescence. In such an embodiment, the release of nucleotides in a process of the invention is ascertained by a determination of a difference in the length of the polynucleotide probe, for example, by capillary electrophoresis imaged by a fluorescent tag at the 5' terminus of the probe or in a region other than the 3'-terminal region.

In an alternative embodiment the analytical output is obtained by mass spectrometry. It is preferred here that an identifier nucleotide be a nucleotide analog or a labeled nucleotide and have a molecular mass that is different from the mass of a usual form of that nucleotide, although a difference in mass is not required. It is also noted that with a fluorescently labeled identifier nucleotide, the analytical output is alternatively obtained by mass spectrometry. It is also contemplated that the analysis of released nucleotide be conducted by ascertaining the difference in mass of the probe after a depolymerization step of a process of the invention.

In another alternative embodiment, the analytical output is obtained by absorbance spectroscopy. Such analysis monitors the absorbance of light in the ultraviolet and visible regions of the spectrum to determine the presence of absorbing species. In one aspect of such a process, released nucleotides are separated from hybridized nucleic acid and other polynucleotides by chromatography (e.g. HPLC or GC) or electrophoresis (e.g. PAGE or capillary electrophoresis). Either the released identifier nucleotide or the remainder of the probe is analyzed to ascertain the release of the identifier nucleotide in a process of the invention. In another aspect of such a process a label may be incorporated in the analyzed nucleic acid.

Another embodiment of the invention is a kit for determining the presence or absence of a single or a plurality of predetermined nucleic acid target sequences in a nucleic acid sample. Such a kit comprises: (A) a purified and isolated enzyme whose activity is to release one or more nucleotides from the 3' terminus of a hybridized nucleic acid probe; and (B) pyrophosphate. A contemplated kit optionally further comprises a nucleic acid probe, said nucleic acid probe being complementary to a nucleic acid target sequence and comprising an identifier nucleotide.

A contemplated kit optionally further comprises a nucleic acid label. In some embodiments of a kit or composition, the identifier nucleotide comprises a fluorescent label and the probe optionally further comprises a fluorescence quencher or enhancer molecule. In other embodiments of a kit or composition, the identifier nucleotide comprises a non-natural nucleotide analog.

The present invention has many benefits and advantages, several of which are listed below.

One benefit of the invention is that, in some embodiments, nucleic acid hybrids can be detected with very high levels of sensitivity without the need for radiochemicals or electrophoresis.

An advantage of the invention is that quantitative information can be obtained about the amount of a target nucleic acid sequence in a sample.

A further benefit of the invention is that the presence or absence of a number of target nucleic acid sequences can be determined in the same assay.

Yet another advantage of the invention is that the results of multiple assays in one reaction may be distinguishable.

Still another benefit of the invention is its flexibility of use in many different types of applications and assays including, but not limited to, detection of mutations, translocations, and SNPs in nucleic acid (including those associated with genetic disease), determination of viral load, species identification, sample contamination, and analysis of forensic samples.

Still further benefits and advantages of the invention will become apparent from the specification and claims that follow.

Definitions

To facilitate understanding of the invention, a number of terms are defined below.

"Nucleoside", as used herein, refers to a compound consisting of a purine [guanine (G) or adenine (A)] or pyrimidine [thymine (T), uridine (U) or cytidine (C)] base covalently linked to a pentose, whereas "nucleotide" refers to a nucleoside phosphorylated at one of its pentose hydroxyl groups. "XTP", "XDP" and "XMP" are generic designations for ribonucleotides and deoxyribonucleotides, wherein the "TP" stands for triphosphate, "DP" stands for diphosphate, and "IMP" stands for monophosphate, in conformity with standard usage in the art. Subgeneric designations for ribonucleotides are "NMP", "NDP" or "NTP", and subgeneric designations for deoxyribonucleotides are "dNMP", "dNMP" or "dNTP". Also included as "nucleoside", as used herein, are materials that are commonly used as substitutes for the nucleosides above such as modified forms of these bases (e.g. methyl guanine) or synthetic materials well known in such uses in the art, such as inosine.

A "nucleic acid," as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence; i.e., a linear order of nucleotides. A "polynucleotide," as used herein, is a nucleic acid containing a sequence that is greater than about 100 nucleotides in length. An "oligonucleotide," as used herein, is a short polynucleotide or a portion of a polynucleotide. An oligonucleotide typically contains a sequence of about two to about one hundred bases. The word "oligo" is sometimes used in place of the word "oligonucleotide".

A base "position" as used herein refers to the location of a given base or nucleotide residue within a nucleic acid.

A "nucleic acid of interest," as used herein, is any particular nucleic acid one desires to study in a sample.

The term "isolated" when used in relation to a nucleic acid or protein, refers to a nucleic acid sequence or protein that is identified and separated from at least one contaminant (nucleic acid or protein, respectively) with which it is ordinarily associated in its natural source. Isolated nucleic acid or protein is present in a form or setting that is different from that in which it is found in nature. In contrast, non-isolated nucleic acids or proteins are found in the state they exist in nature.

As used herein, the term "purified" or "to purify" means the result of any process which removes some contaminants from the component of interest, such as a protein or nucleic acid. The percent of a purified component is thereby increased in the sample.

Nucleic acids are known to contain different types of mutations. As used herein, a "point" mutation refers to an alteration in the sequence of a nucleotide at a single base position. A "lesion", as used herein, refers to site within a nucleic acid where one or more bases are mutated by deletion or insertion, so that the nucleic acid sequence differs from the wild-type sequence.

A "single nucleotide polymorphism" or SNP, as used herein, is a variation from the most frequently occurring base at a particular nucleic acid position.

Homologous genes or alleles from different species are also known to vary in sequence. Regions of homologous genes or alleles from different species can be essentially identical in sequence. Such regions are referred to herein as "regions of identity." It is contemplated herein that a "region of substantial identity" can contain some "mismatches," where bases at the same position in the region of identity are different. This base position is referred to herein as "mismatch position."

DNA molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus. As used herein, a nucleic acid sequence, even if internal to a larger oligonucleotide or polynucleotide, also can be said to have 5'- and 3'- ends. For example, a gene sequence located within a larger chromosome sequence can still be said to have a 5'- and 3'-end.

As used herein, the 3'-terminal region of the nucleic acid probe refers to the region of the probe including nucleotides within about 10 residues from the 3'-terminal position.

As used herein, the term "target nucleic acid" or "nucleic acid target" refers to a particular nucleic acid sequence of interest. Thus, the "target" can exist in the presence of other nucleic acid molecules or within a larger nucleic acid molecule.

As used herein, the term "nucleic acid probe" refers to an oligonucleotide or polynucleotide that is capable of hybridizing to another nucleic acid of interest under low stringency conditions. A nucleic acid probe may occur naturally as in a purified restriction digest or be produced synthetically, recombinantly or by PCR amplification. As used herein, the term "nucleic acid probe" refers to the oligonucleotide or polynucleotide used in a method of the present invention. That same oligonucleotide could also be used, for example, in a PCR method as a primer for polymerization, but as used herein, that oligonucleotide would then be referred to as a "primer". In some embodiments herein, oligonucleotides or polynucleotides contain a modified linkage such as a phosphorothioate bond.

As used herein, the terms "complementary" or "complementarity" are used in reference to nucleic acids (i.e., a sequence of nucleotides) related by the well-known base-pairing rules that A pairs with T and C pairs with G. For example, the sequence 5'-A-G-T-3', is complementary to the sequence 3'-T-C-A-5'. Complementarity can be "partial," in which only some of the nucleic acid bases are matched according to the base pairing rules. On the other hand, there may be "complete" or "total" complementarity between the nucleic acid strands when all of the bases are matched according to base pairing rules. The degree of complementarity between nucleic acid strands has significant effects on the efficiency and strength of hybridization between nucleic acid strands as known well in the art. This is of particular importance in detection methods that depend upon binding between nucleic acids, such as those of the invention. The term "substantially complementary" refers to any probe that can hybridize to either or both strands of the target nucleic acid sequence under conditions of low stringency as described below or, preferably, in polymerase reaction buffer (Promega, M195A) heated to 95° C. and then cooled to room temperature. As used herein, when the nucleic acid probe is referred to as partially or totally complementary to the target nucleic acid, that refers to the 3'-terminal region of the probe (i.e. within about 10 nucleotides of the 3'-terminal nucleotide position).

The term "hybridization" is used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved affected by such conditions as the concentration of salts, the $T_m$ (melting temperature) of the formed hybrid, the presence of other components (e.g., the presence or absence of polyethylene glycol), the molarity of the hybridizing strands and the G:C content of the nucleic acid strands.

The term "$T_m$" is used in reference to the "melting temperature". The melting temperature is the temperature at which 50% of a population of double-stranded nucleic acid molecules becomes dissociated into single strands. The equations for calculating the $T_m$ of nucleic acids are well-known in the art. The $T_m$ of a hybrid nucleic acid is often estimated using a formula adopted from hybridization assays in 1 M salt, and commonly used for calculating $T_m$ for PCR primers: $T_m$=[(number of A+T)×2° C.+(number of G+C)×4° C.]. C. R. Newton et al. PCR, $2^{nd}$ Ed., Springer-Verlag (New York: 1997), p. 24. This formula was found to be inaccurate for primers longer that 20 nucleotides. Id. Other more sophisticated computations exist in the art that take structural, as well as, sequence characteristics into account for the calculation of $T_m$. A calculated $T_m$ is merely an estimate; the optimum temperature is commonly determined empirically.

The term "homology", as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous".

When used in reference to a double-stranded nucleic acid sequence such as a cDNA or genomic clone, the term "substantially homologous", as used herein, refers to a probe that can hybridize to a strand of the double-stranded nucleic acid sequence under conditions of low stringency.

When used in reference to a single-stranded nucleic acid sequence, the term "substantially homologous", as used herein, refers to a probe that can hybridize to (i.e., is the complement of) the single-stranded nucleic acid template sequence under conditions of low stringency.

The term "interrogation position", as used herein, refers to the location of a given base of interest within a nucleic acid probe. For example, in the analysis of SNPs, the "interrogation position" in the probe is in the position that would be complementary to the single nucleotide of the target that may be altered from wild type. The analytical output from a method of the invention provides information about a nucleic acid residue of the target nucleic acid that is complementary to an interrogation position of the probe. An interrogation position is within about ten bases of the actual 3'-terminal nucleotide of the nucleic acid probe, although not necessarily at the 3'-terminal nucleotide position. The interrogation position of the target nucleic acid sequence is opposite the interrogation position of the probe, when the target and probe nucleic acids are hybridized.

The term "identifier nucleotide", as used herein, refers to a nucleotide whose presence is to be detected in a process of the invention to identify that a depolymerization reaction has occurred. The particular application of a method of the invention affects which residues are considered an identifier nucleotide. For a method using ATP detection (e.g. luciferase/luciferin or NADH) wherein, during analysis, all nucleotides released in the depolymerization are "converted" to ATP with an enzyme such as NDPK in the presence of ADP and use of the released nucleotide as the phosphate donor, all nucleotides released are identifier nucleotides. Similarly, for a method using absorbance detection that does not distinguish between nucleotides, all released nucleotides are identifier nucleotides. For a mass spectrometric detection wherein all the released nucleotides are analyzed, all released nucleotides can be identifier nucleotides; alternatively a particular nucleotide (e.g. a nucleotide analog having a distinctive mass) can be detected. For fluorescence detection, a fluorescently-labeled nucleotide is an identifier nucleotide. The nucleotide can be labeled prior to or after release from the nucleic acid. In some cases, the release of identifier nucleotide is deduced by analyzing the remainder of the probe after a depolymerization step of the invention. Such analysis is generally by a determination of the size or mass of the remaining probe and can be by any of the described analytical methods (e.g. a fluorescent tag on the 5'-terminus of the probe to monitor its molecular weight following capillary electrophoresis).

The term "sample", as used herein, is used in its broadest sense. A sample suspected of containing a nucleic acid can comprise a cell, chromosomes isolated from a cell (e.g., a spread of metaphase chromosomes), genomic DNA, RNA, cDNA and the like.

The term "detection", as used herein, refers to quantitatively or qualitatively identifying a nucleotide or nucleic acid within a sample.

The term "depolymerization", as used herein, refers to the removal of a nucleotide from the 3' end of a nucleic acid.

For other definitions, please see the parent applications recited above and incorporated herein by reference.

DETAILED DESCRIPTION OF THE INVENTION

A method of this invention is used to determine the presence or absence of at least one predetermined (known)

nucleic acid target sequence in a nucleic acid sample. The focus of the embodiments discussed herein is the variety of methods of analyzing for released nucleotide in a method of the invention. A nucleic acid target is "predetermined" in that its sequence must be known in order to design a probe that hybridizes with that target. However, it should be noted that a nucleic acid target sequence, as used with respect to certain embodiments of this invention, merely act as a reporter to signal the presence or absence of a different nucleic acid whose presence or absence is desired to be determined. Furthermore, other embodiments of the invention are useful in determining the identity of a base within a target where only enough of the sequence is known to design a probe that hybridizes to that target with partial complementarity at the 3'-terminal region of the probe.

Such a method utilizes an enzyme that depolymerizes the 3'-terminus of an oligonucleotide probe hybridized to the nucleic acid target sequence to release one or more identifier nucleotides whose presence or absence is then determined as an analytical output that indicates the presence or absence of the target sequence. The depolymerizing enzyme is discussed in more detail hereinafter.

A nucleic acid probe is provided to be partially or totally complementary to the predetermined nucleic acid target sequence. Thus, a nucleic acid target sequence is a portion of nucleic acid sample with which the probe hybridizes if that target sequence is present in the sample.

As mentioned above, in one contemplated embodiment, a nucleic acid target acts as a "reporter" for the presence of a different nucleic acid of interest. In such embodiments, methods that rely on hybridization of a primer to a nucleic acid of interest are used to amplify a portion of that nucleic acid and/or a nucleic acid target to provide analytical output in an assay or kit of the invention. These methods are discussed in the parent application in greater detail and include rolling circle replication and polymerase chain reaction.

In one embodiment, a treated sample is formed by admixing a sample to be assayed with one or more nucleic acid probes. The treated sample contains a target:probe nucleic acid hybrid when the target complementary to the added probe is present. The admixing of the nucleic acid sample and probe(s) is typically carried out under low stringency hybridizing conditions to form a hybridization composition. In such a hybridization composition, the 3'-terminal region of the nucleic acid probe(s) (i) hybridizes with partial or total complementarity to a nucleic acid target sequence that may be present in the sample; and (ii) includes an identifier nucleotide in the 3'-terminal region.

Preferably, the nucleic acid probe is designed to not hybridize with itself to form a hairpin structure in such a way as to interfere with hybridization of the 3'-terminal region of the probe to the target nucleic acid. Parameters guiding primer design for PCR and other nucleic acid hybridization techniques are well known in the art and are applicable to probe design for the present invention.

The hybridization composition is maintained under hybridizing conditions (discussed hereinafter) for a time period sufficient to form a treated sample that may contain a predetermined nucleic acid target sequence hybridized with a nucleic acid probe.

In the event that the sample to be assayed does not contain a target sequence to which the probe hybridizes, no hybridization takes place upon forming a treated sample. However, in an embodiment wherein a treated sample is formed, the sample is still admixed with the probe(s) and maintained under conditions that would permit hybrid formation if a nucleic acid target is present. When a method of the present invention is used to determine whether a particular target sequence is present or absent in a sample to be assayed, the resulting treated sample may not contain a substrate for the depolymerizing enzymes of the present invention. As a result, a 3' terminal region identifier nucleotide is not released and the analytical output is at or near background levels.

In one embodiment of the invention, a nucleic acid hybrid is formed, and the depolymerization substrate is already present without going through the steps of admixing probe (s) and maintaining under hybridizing conditions. Thus, the "treated sample" is preformed in one embodiment.

The treated sample is admixed with a depolymerizing amount of an enzyme whose activity is to release one or more identifier nucleotides from the 3'-terminal region of the probe that is hybridized to the nucleic acid target to form a depolymerization reaction mixture. The choice of enzyme used in the process determines if a match or mismatch at the 3'-terminal nucleotide results in release of that 3'-terminal nucleotide. Further information regarding specific enzymes and depolymerization reaction conditions is discussed in detail hereinafter, and also in the parent case.

The depolymerization reaction mixture is maintained under depolymerizing conditions for a time period sufficient to permit the enzyme to depolymerize hybridized nucleic acid and release identifier nucleotides therefrom to form a treated reaction mixture.

The presence or absence of released identifier nucleotides is then determined to obtain an analytical output. The analytical output indicates the presence or absence of at least the one nucleic acid target sequence.

Some processes of the invention are concerned with the degree of hybridization of the target to the 3'-terminal region of the probe. Examples in the parent application, U.S. patent application Ser. No. 09/358,972, filed Jul. 21, 1999, show that the distinction between a matched and mismatched base becomes less notable as a single mismatch is at a position further upstream from the 3'-terminal region position. There is very little discrimination between a match and mismatch when a single mismatch is ten to twelve residues from the 3'-terminal nucleotide position, whereas great discrimination is observed when a single mismatch is at the 3'-terminus. Therefore, when the degree of complementarity (partial or total complementarity) of a nucleic acid probe hybridized to a target nucleic acid sequence is referred to herein in regard to an identifier nucleotide, this is to be understood to be referring to within the 3'-terminal region, up to about ten residues of the 3'-terminal position.

Hybridization conditions are empirically ascertained for a control sample for various time periods, pH values, temperatures, nucleic acid probe/target combinations, concentrations and the like. Exemplary maintenance times and conditions are provided in the specific examples hereinafter and typically reflect low stringency hybridization conditions. In practice, once a suitable set of hybridization conditions and maintenance time periods are known for a given set of probes, an assay using those conditions provides the correct result if the nucleic acid target sequence is present. Typical maintenance times are about 5 to about 60 minutes.

The conditions and considerations with respect to hybridization of PCR primers to template nucleic acid in PCR are applicable to the hybridization of nucleic acid probes to target sequences in a process of the invention. Such hybridization conditions are well known in the art, and are a matter of routine experimentation depending on factors including the sequence of the nucleic acid probe and the target nucleic acid [sequence identity (homology), length and G+C content] molar amounts of nucleic acid present, buffer, salt content and duplex $T_m$ among other variables.

Processes of the invention are sensitive and hybridization conditions of low stringency (e.g. temperature of 0–4° C.) are sufficient, but moderate stringency conditions (i.e. temperatures of 40–60° C.) also permit hybridization and provide acceptable results. This is true for all processes of the invention.

In one contemplated embodiment of the invention, the enzyme whose activity is to depolymerize hybridized nucleic acid to release nucleotides from the probe 3'-terminal end is a template-dependent polymerase. In such an embodiment, the reverse of a polymerase reaction (pryophosphorolysis) is used to depolymerize a nucleic acid probe, and the identifier nucleotide is released most efficiently when the 3'-terminal nucleotide of the nucleic acid probe hybridizes with total complementarity to its nucleic acid target sequence. Thus, in an embodiment using the reverse of a polymerase reaction to depolymerize nucleic acid hybrid, a signal confirms the presence of a nucleic acid target sequence that has a sequence complementary to the nucleic acid probe in order to be detected by the process of the invention. In an embodiment using fluorescent labels along with a fluorescence enhancer or fluorescence quencher the depolymerization may be observed by a change in the fluorescence emission as discussed below.

Various template-dependent polymerases useful in a process or kit of the invention are known in the art, including thermostable polymerases. Preferred template-dependent polymerases are Taq polymerase, Tne polymerase, Tne triple mutant polymerase, Tth polymerase, Tvu polymerase, Ath polymerase, T4 DNA polymerase, Klenow fragment, Klenow exo minus, E. coli DNA polymerase I, AMV reverse transcriptase, MMLV reverse transcriptase, or poly(A) polymerase. Particularly preferred template-dependent polymerases are Tne polymerase, Tne triple mutant polymerase, Klenow exo minus, MMLV reverse transcriptase, with Tne triple mutant polymerase being most particularly preferred. For RNA substrates, AMV reverse transcriptase, MMLV reverse transcriptase, or poly(A) polymerase are particularly preferred. The pyrophosphorolysis reaction and enzymes are discussed in more detail in the parent application cited above and is incorporated herein by reference.

It can be beneficial to carry out a contemplated method at elevated temperatures, e.g., about 50° C. to about 90° C. The Tne triple mutant DNA polymerase is described in detail in WO 96/41014, whose disclosures are incorporated herein by reference, and its 610 residue amino acid sequence is provided as SEQ ID NO:35 of that document. That enzyme is referred to in WO 96/41014 as Tne 284 (D323A,D389A).

Briefly, that enzyme is a triple mutant of the polymerase encoded by the thermophilic eubacterium *Thermotoga neoapolitanta* (ATCC 49049). The amino-terminal 283 resides of the native sequence are deleted and the aspartic acid residues at positions 323 and 389 of the native sequence are replaced by alanine residues in this recombinant enzyme. This recombinant enzyme is thus a deletion and replacement mutant of the native enzyme.

Deletion of the amino-terminal sequence removes the 5' exonuclease activity of the native enzyme, whereas replacement of the two aspartic acid residues removes a magnesium binding site whose presence facilitates exonuclease activity, and this triple mutant also exhibited no 3' exonuclease activity relative to the recombinant native enzyme. This triple mutant enzyme exhibited a half-life at 97.5° C. of 66 minutes as compared to the full length recombinant enzyme that exhibited a half-life of only 5 minutes at that temperature.

In an embodiment that uses a 3' to 5' exonuclease activity of a polymerase to depolymerize a nucleic acid probe, an identifier nucleotide is released when the 3'-terminal residue of the nucleic acid probe is mismatched and therefore there is only partial complementarity of the 3'-terminal region of the nucleic acid probe to its nucleic acid target sequence. In this embodiment, to minimize background, the hybrid is typically purified from the unannealed nucleic acid prior to the enzyme reaction, which releases identifier nucleotides. A signal confirms the presence of a nucleic acid target sequence that is not totally complementary to the nucleic acid probe.

Various polymerases with 3' to 5' exonuclease activity useful in this embodiment of the invention that uses a 3' to 5' exonuclease activity of a polymerase, to depolymerize a nucleic acid probe are known in the art, also including thermostable polymerases. Such polymerases include *E. coli* DNA polymerase I, Klenow or T4 DNA polymerase. Preferred polymerases with 3' to 5' exonuclease activity useful in this embodiment of the invention are Klenow or T4 DNA polymerase. The depolymerization reaction that uses a 3' to 5' exonuclease activity of a polymerase and enzymes are discussed in more detail in the parent application cited above and is incorporated herein by reference.

In an embodiment that uses a 3' to 5' exonuclease activity of Exonuclease III to depolymerize a nucleic acid probe, an identifier nucleotide is released when the 3'-terminal residue of the nucleic acid probe is matched to the target nucleic acid. A signal confirms the presence of a nucleic acid target that is complementary at the released identifier nucleotide. Preferred enzymes for this embodiment are Exonuclease III, S1 nuclease, nuclease BAL 31, mung bean nuclease, and ribonuclease H, most preferably, Exonuclease III. The depolymerization reaction that uses a 3' to 5' exonuclease activity and the enzymes are discussed in more detail in the parent application cited above and is incorporated herein by reference.

It is thus seen that hybridization and depolymerization can lead to the release of an indicator nucleotide or to little or no release of such a nucleotide, depending upon whether the probe:target hybrid is matched or mismatched at the 3'-terminal region. This is also dependent on the type of enzyme used and the type of end, matched or mismatched, that the enzyme requires as a substrate for depolymerization activity. Exemplary depolymerizing conditions are provided in the Examples that follow, and are expanded upon in the parent application, U.S. patent application Ser. No. 09/358,972, incorporated herein by reference.

The magnitude of a contemplated analytical output under defined conditions is dependent upon the amount of nucleotide released. Where an identifier nucleotide is released, an analytical output can be provided that has a value greater than the background output. Where an identifier nucleotide is not released either because the target sequence was not present in the original sample or because the probe and depolymerizing enzyme chosen do not provide release of a 3'-terminal nucleotide when the target is present, or if the match/mismatch state of the 3'-terminal nucleotide did not match that required for the enzyme used to release a 3'-terminal nucleotide, the analytical output is substantially at a background level.

A contemplated method is particularly useful in a multiplex assay environment in which a plurality of probes is utilized to determine whether one or more of a plurality of predetermined nucleic acid target sequences is present or absent in a sample.

In some preferred multiplex embodiments, the output is distinguishable, i.e. it is possible to determine which probe:target nucleic acid hybrids contributed to the analytical output. The mass spectrometric and fluorescence spectroscopic embodiments of the present invention are particularly preferred in a distinguishable multiplex embodiment of the present invention, preferably through the use of unique identifier nucleotides.

One useful area for multiplex assays is in screening assays where the usual analytical output indicates that the sought-after gene is absent. In one illustrative embodiment, a nucleic acid sample is screened for the presence of a plurality of predetermined mutant genes. In this embodiment, the mutants usually are not present and the analytical output is, for example, at about background levels except where a mutation is present. In another embodiment, a plurality of samples is examined for the presence or absence of microbe-specific genes. Here, again, where a population of healthy individuals, animals, or presumably sterile food is sampled, the absence of the sought-after genes provides an analytical output that is about background levels, and only in the rare instance of a microbe-specific gene being present does a greater than background output appear.

In a multiplex embodiment of the above process, the sample is admixed with a plurality of different nucleic acid probes, preferably after amplification of the multiple nucleic acid targets as needed. Multi-well plates common in the art presently have volumes of 100 μL for 96 well plates, and 10 μL for a 384 well plates. The 100 μL volume is preferred for most embodiments of the present invention. In an embodiment of the invention lacking unique identifier nucleotides, the analytical output for a certain result with one of the probes is distinguishable from the analytical output from the opposite result with all of the probes.

In alternative multiplex embodiments, ATP is produced via nucleotide diphosphate kinase (NDPK) use of released nucleotides as phosphate donors in the presence of ADP. In these embodiments, if increased sensitivity is required, the ATP molecules can be amplified, for example by the addition of adenylate kinase and exogenous AMP. ATP amplification is discussed in more detail in the parent application, incorporated herein by reference. The ATP produced is detected by a fluorescence spectroscopic NADH detection system in one embodiment, or an absorbance spectroscopic glucose-6-phosphate system in another embodiment. Detection of ATP using luminescence spectroscopy is discussed in greater detail in the parent application. In still another embodiment of the present invention, the pyrophosphate transferring step and the phosphate transferring step are performed in a single pot reaction.

In a contemplated multiplex embodiment, information about the presence or absence of a plurality of nucleic acid target sequences is determined using a process of the invention on a single nucleic acid sample, by admixing the sample with a plurality of nucleic acid probes for the various nucleic acid targets.

Various useful groups of nucleic acid targets and exemplary probe nucleic acid sequences are described in the parent application listed above and incorporated herein by reference. These include groups of human pathogens, animal pathogens, human and animal genetic sequences that correlate to various diseases or medical conditions, plant pathogens, and markers for genetically modified organisms, including plants.

A. Analytical Output

The analytical output is obtained by detection of the released products, either the released identifier nucleotides or the remainder of the probe, preferably the identifier nucleotide. The fact that one or more nucleotides were released (a qualitative determination), or even the number of nucleotides released (a quantitative determination) can be deduced through examination of the released nucleotides or the probe after depolymerization.

The decision of whether to analyze for released identifier nucleotide or the remaining probe is based upon the embodiment of the invention selected, and where a label is placed. In several embodiments, a conveniently detectable label is placed on the nucleic acid probe, preferably in the 3'-terminal region where the labeled nucleotide is depolymerized as a released identifier nucleotide, but alternatively in a region other than the 3'-terminal region, in such a manner that the labeled nucleotide remains on the probe after depolymerization.

In an alternative contemplated embodiment, an identifier nucleotide is located in the nucleic acid target, and a probe is designed such that the 5'-terminus of the probe overhangs the 3'-terminus of the nucleic acid target. In this case, depolymerization of the hybrid nucleic acid from the 3' terminus will result in a release of identifier nucleotide from the nucleic acid target.

For examination of the depolymerized nucleic acid, the determination of the size of an oligonucleotide is well known in the art. For example gel separation and chromatographic separations are well known. Gel imaging techniques take advantage of fluorescence and absorbance spectroscopy as well as radiographic methods. Mass spectrometry of oligonucleotides is also becoming more common.

Exemplary detection systems for detecting either released identifier nucleotide or the remaining probe include mass spectrometry, fluorescence spectroscopy and absorbance spectroscopy. These detection methods are equally useful for the detection of the released identifier nucleotide as they are for the remaining probe, depending on where the label is (if a label is used) or on size differential. For example, in cases where the size of the remaining nucleic acid probe after depolymerization is not easily distinguishable from the size before depolymerization, one may choose to focus on the determination of the released nucleotides. The various detection systems are discussed hereinbelow.

1. Mass Spectrometric Analysis

In one aspect of the invention, the presence of released nucleotide is analyzed via mass spectrometry. In an embodiment of a method using mass spectrometry, the treated reaction mixture is ionized in a manner such that all components of the treated reaction mixture in the molecular weight range of the released identifier nucleotide or the remaining probe are measured. Very small differences in molecular weight can be detected using mass spectrographic methods (different isotopes of the same atom are detectable). Thus, any variation from a natural nucleic acid, including a single atom substitution (e.g. a fluorine in place of a hydrogen atom or a replacement of a hydrogen by a deuterium atom) in the identifier nucleotide gives rise to a detectable difference in analytical output.

Nucleic acid analogs chosen for use in this aspect of the invention should not interfere with either the hybridization of the nucleic acid probe or depolymerization of the hybridized probe. Various nucleotide analogs and nucleic acid labels such as pendant fluorescent groups are well known in the art, and are known to not interfere with hybridization or polymerization. Such nucleotides and labels are commercially available and are useful in practicing the invention.

Mass spectrometry can discriminate between individual nucleotides. For example, if the 3'-identifier nucleotide used in the instant aspect were a G nucleotide, mass spectrometry can be used to detect the release of that G nucleotide in a method of the present invention. Similarly, mass spectrometry can be used to detect the release of an A, T or C nucleotide, based on the differences in atomic weight of these compounds.

As mentioned briefly above, a mass spectrometric analysis of the nucleic acid polymers in the treated sample can be used either to identify released nucleotides or to determine whether a nucleic acid probe or target was depolymerized by ascertaining the size of the remaining nucleic acid polymer. Using mass spectrometry, the size of the probes after treatment of hybridized samples with a depolymerizing enzyme can be determined to discover whether a given probe has been depolymerized. If unique probe sizes are used in a multiplex embodiment, it is possible to distinguish which probes were depolymerized. No labels are necessary for the determination of size differences based on depolymerization, however the use of labels comprising nucleotide analogs is contemplated and can be helpful in distinguishing multiple probes. Such labels are preferably at other than the 3'-terminal region in this embodiment. It is contemplated that a label on the probe also encompasses a non-complementary nucleic acid sequence at the 5'-terminus of the region of the probe that is complementary to the nucleic acid target. Alternatively, a label on the 5'-terminus of a probe is another molecule altogether, that isn't even a nucleotide, but merely that acts as a weight marker.

In a multiplex embodiment of the present invention, mass spectrometry can be used to resolve the presence of one or more identifier nucleotides or probe sizes in such a manner as to distinguish which probe:target nucleic acid nucleic acid hybrids were depolymerized. Preferably, this is done using multiple different identifier nucleotides in the various nucleic acid probes. Different identifier nucleotides have distinguishably different labels, or they have 3'-terminal regions with identifiably different nucleotides (e.g. only the wild type probe has G residues in the 3'-terminal region). Using such a technique, the presence of the different released identifier nucleotides is direct evidence of the presence of the nucleic acid target sequences.

In a particularly useful aspect of this embodiment, a mass spectral technique referred to as DIOS (desorption/ionization on silicon) was recently reported by Wei et al., *Nature*, 399:243 (1999), that can accurately perform one or multiple assays on picogram or attogram amounts using commercially available mass spectrographs adapted with a specialized porous silicon sample well. The older, well known, MALDI mass spectrographic assay and electrospray ionization mass spectrometry techniques can also be utilized (Liu et al., *Anal Chem.,* 68:3295 (1996), Greig et al., Rapic Commun. Mass Spec. 10:47 (1996)).

Matrix-Assisted Laser Desorption Ionization Time of Flight Mass Spectrometry (MALDI-TOF MS) is useful for analyzing small amounts of nucleic acid (about 5 femtomoles) with very high resolution (about one dalton). As the size of a nucleic acid polymer increases, the sensitivity and mass resolution of its detection decreases, so that one cited current upper practical limit for MALDI-TOF MS of DNA is between about 50 to 100 nucleotide bases in size. The sensitivity and resolution is decreased for nucleic acid polymers longer than 500 bases. During the laser desorption ionization process in a MALDI-TOF mass analysis, a probe target hybrid will fully dissociate.

A process of the present invention differs significantly from the processes disclosed in U.S. Pat. No. 5,885,775, which requires a dideoxy-terminal extension step followed by 3'-terminal exonuclease digestion of the extension product to provide additional nucleotides of varying lengths (i.e. more than the dideoxy-terminations provided). In contrast, processes of the present invention involve depolymerization of the probe in a probe/target hybrid, and there is no preceding step of extension of the probe as a polymerase primer.

2. Fluorescence Spectroscopic Analysis

In some contemplated embodiments with fluorescence spectroscopic analysis, the identifier nucleotide includes a fluorescent label. In one embodiment when the nucleotide has a fluorescent label, the analytical output is obtained by fluorescence spectroscopy. In an alternative embodiment when the nucleotide has a fluorescent label, the analytical output is obtained by mass spectrometry discussed before, because the presence of an added fluorophore alters the molecular weight of the identifier nucleotide.

In a preferred embodiment of the invention, the fluorescent label is part of a fluorescently-labeled analog of a nucleotide and that nucleotide is incorporated into the probe, preferably in the 3' terminal region to be released as the identifier nucleotide. Alternatively, the fluorescently-labeled nucleotide analog is incorporated into the probe in other than the 3'-terminal region to be analyzed as the part of the probe left after treatment with a depolymerizing enzyme.

In an alternative embodiment, a nucleic acid probe comprises a fluorescent label, either in the 3'-terminal region or not in the 3'-terminal region, and the probe further comprises a second fluorophore, capable of acting either as a fluorescence quencher or a fluorescence enhancer. Release of either the fluorescent label itself, or the fluroscence quencher/enhancer results in a change in fluorescence of the sample to generate an analytical output signaling the presence or absence of the nucleic acid target. This embodiment is discussed in more detail below.

Fluorescent nucleotide analogs are widely known and commercially available from several sources. An exemplary source is NEN™ Life Science Products (Boston, Mass.), which offers dideoxy-, deoxy-, and ribonucleotide analogs a labeled with fluorescein, coumarin, tetramethylrhodamine, naphthofluorescein, pyrene, Texas Red®, and Lissamine™. Other suppliers include Amersham Pharmacia Biotech (Uppsala, Sweden; Piscataway, N.J.) and MBI Fermentas, Inc. (Amherst, N.Y.).

An advantage to using fluorescent labels and fluorescence spectroscopy analysis is that there are multiple different labels available. Such different labels can be particularly useful in a multiplex embodiment of the invention. Different fluorescent labels are used in different probes, so that the detection of a particular fluorescently-labeled nucleotide analog as a released identifier nucleotide can be distinguished from others and used to deduce which nucleic acid targets are present.

For example, fluorescein has a 488 nm excitation and 520 nm emission wavelength, whereas rhodamine (in the form of tetramethyl rhodamine) has 550 nm excitation and 575 nm emission wavelength. A fluorescence detector provides an excitation source and an emission detector. The emission wavelengths of 520 nm and 575 nm are easily distinguishable using fluorescence spectroscopy.

On a per molecule basis, fluorescence spectroscopy is about 10-fold more sensitive than absorbance spectroscopy. A very wide variety of fluorescence spectroscopy-based detectors are commercially available for reading fluorescence values of single tubes, flow cells and multi-well plates, among others. For example, Labsystems Multiskan models of microplate readers are widely available with a spectral range of 400 to 750 nm, and filters for 340, 405, 414, 450, 492, 540, 620, and 690 nm (e.g. Fisher Scientific, Pittsburgh, Pa.).

It is contemplated that a depolymerization reaction product, such as a released identifier nucleotide or the probe that remains, can be labeled before or after depolymerization using cross-linking chemistry well known in the art with commercially available reagents. For example, fluorescein isothiocyanate and rhodamine B isothiocyanate are both available from Aldrich Chemical Company (Milwaukee, Wis.). References to use of fluorescein isothiocyanate in labeling biological molecules include *Nature,* 193:167 (1962); *Meth. Enzymol.,* 26:28 (1972); *Anal. Biochem.,* 57:227 (1974); *Proc. Natl. Acad. Sci., USA,* 72:459 (1975).

It is contemplated that for many embodiments of the invention, it is useful to separate released fluorescent identifier nucleotides from those remaining bound to an oligonucleotide, such as a probe. Thus, the separation techniques well known in the art and discussed herein are useful with such an embodiment, including HPLC fitted with a fluorescence detector, and the use of magnetic particles. The enhanced sensitivity of fluorescence relative to other spectroscopic techniques can be used to increase the sensitivity of a detection or quantification process of the invention.

Flourescent resonant energy transfer (FRET) is a form of molecular energy transfer by which energy is passed between a donor molecule and an acceptor molecule. FRET arises from the properties of certain chemical compounds; when excited by exposure to particular wavelengths of light, they emit light (i.e., they fluoresce) at a different wavelength. Such compounds are termed fluorophores. In FRET, energy is passed non-radiatively over a long distance between a donor molecule, which is a fluorophore, and an acceptor molecule. The donor absorbs a photon and transfers energy nonradiatively to the acceptor (reviewed in Clegg, Methods Enzymology 211:353–388 (1992)).

Depending on what kind of fluorophore molecule is being monitored (i.e. a donor or an acceptor), the fluorescence is either quenched or enhanced by a transfer of energy. Resonant overlap of the excitation and emission spectra of two fluorophores enables an energy transfer. Energy transfer also depends on physical factors, such as the orientation and distance between the two fluorophores. Resonant energy transfer is well known in the art, and skilled workers are able to choose compatible pairs for fluorescence quenching or enhancement, along with useful excitation and fluorescence detection wavelengths. The disclosures of U.S. Pat. Nos. 5,691,146; 5,876,930; 5,723,591; 5,348,853; 5,119,801; 5,312,728; 5,962,233; 5,942,283; 5,866,336, discussing such fluorophores, are incorporated herein by reference.

Whether a fluorophore is a donor or an acceptor is defined by its excitation and emission spectra, and the fluorophore with which it is paired. For example, FAM is most efficiently excited by light with a wavelength of 488 nm, and emits light with a spectrum of 500 to 650 nm, and an emission maximum of 525 nm. FAM is a suitable donor fluorophore for use with JOE, TAMRA, and ROX (all of which have excitation maximum at 514 nm).

Molecules that are commonly used in FRET include Fluorescein, 5-carboxyfluorescein (FAM), 2'7' dimethoxy-4'5'-dichloro-6-carbosyfluorescein (JOI), rhodamine, 6-carboxyrhodamine (R6G), N,N,N,N-tetramethyl-6-carboxyrhodamine (TAMRA), 6-carboxy-X-rhodamine (ROX), 4-(4'-dimethylaminophenylazo)benzoic acid (DABCYL), and 5-(2'-aminoethyl)aminonaphthalene-1-sulfonic acid (EDANS).

A fluorescence spectroscopic embodiment of the invention takes advantage of fluorescent resonance energy transfer (FRET). A nucleic acid probe has two fluorophore labels (e.g. A and B) in proximity to one another in the intact probe such that exciting A with a laser will emit light which excites B, resulting in a detectable fluorescent emission from B. Depolymerization of a probe:hybrid duplex according to the invention results in the release of a nucleotide harboring a fluorophore label, such that they are no longer in resonant proximity with one another. The release of nucleotide results in a decrease in the fluorescent emission from B upon laser excitation of A. It is contemplated that the depolmerization process is monitored either in real time (i.e. at multiple time points) or at an end-point (i.e. at a set time after the depolymerization reaction begins). In one contemplated embodiment, both fluorophores are in the 3'-terminal region of the probe. In an alternative contemplated embodiment, one fluorophore is in the 3'-terminal region and a second fluorophore is elsewhere in the probe. The disclosures of U.S. Pat. Nos. 5,348,853; 5,119,801; 5,312,728; 5,962,233; 5,945,283; 5,876,930; 5,723,591; 5,691,146; and 5,866,336 disclosing fluorophore labeled oligonucleotides are incorporated herein by reference.

In a related fluorescence enhancement spectroscopic embodiment, there are two probes that are distinguishable. One probe will be depolymerized on a wild type target, and the other probe will be depolymerized on a mutant target. It is contemplated that the reactions with the two probes can be conducted in a single reaction vessel. In another related multiplex fluorescent enhancement spectroscopic environment, there are multiple distinguishable probes to different nucleic acid targets. Depolymerization results in a decrease in fluorescence.

In an alternative fluorescence quenching spectroscopic embodiment, there are two fluorophores on a probe, one that quenches the fluorescence of the other when they are in proximity with one another. Such interacting fluorescent molecules, including labeled nucleotide analogs are known in the art [Lee et al., *Nucleic Acids Res.,* 21:3761–3766 (1993); Bassler et al., *App. Environ. Microbiol.,* 61:3724–3728 (1995); Livak et al., *PCR Methods Applic.,* 4:357–362 (1995); and Livak et al., *Nature Genet.,* 9:341–342 (1995)] and commercially available, for example 6-carboxy-fluorescein (6-FAM; fluorescence emission observed at 518 nm) and 6-carboxytetramethylrhodamine (TAMRA). Thus, when the probe is intact, the fluorescence of one fluorophore is quenched. Depolymerization of the probe results in removal of the quencher from quenching proximity, resulting in an observed increase in fluorescence. The multiplex embodiments discussed above with fluorescence enhancement are also contemplated for this embodiment with fluorescence quenching, once again with real-time or end-point fluorescence detection.

In some fluorescence quenching or fluorescence enhancement embodiments, the analytical output is conveniently observed from the ratio of emission of the two fluorophores.

It is further contemplated that the depolymerization/fluorescence detection embodiments can be carried out using instrumentation currently available or available in the future, such as commercial spectrofluorometric thermal cyclers, including the portable model Advanced Nucleic Acid Analyzer disclosed by P. Belgrader et al., *Science*, 284:449–450 (Apr. 16, 1999); and sequence detectors (e.g. from ABI Prism 7700 Sequence Detector) that permit measurement of fluorescent spectra of thermal cycler multi-well plates.

3. Absorbance Spectroscopic Analysis

An absorbance spectrographic analysis is contemplated to provide an analytical output, thereby providing for the determination of the presence or absence released identifier nucleotide, and indicates the presence or absence of said nucleic acid target sequence.

One absorbance spectroscopic embodiment contemplates the chromatographic separation with light absorbance detection of a reaction mixture that has been treated with a depolymerizing amount of an enzyme whose activity is to release one or more nucleotides from the 3'-terminus of a hybridized nucleic acid.

In an illustrative embodiment, a multiplexed assay for the presence of several different nucleic acid target sequences in a sample is analyzed by absorbance spectroscopy. Several labeled probes to various nucleic acid target sequences are added to a nucleic acid sample. The labels on the probes may be various nucleotide analogs, a different one for each probe. A depolymerizing enzyme is added, such as Klenow exo–, releasing the labeled nucleotides and other nucleotides from the 3'-termini of probes hybridized to target sequences when the 3'terminal nucleotide is matched.

The reaction solution is loaded onto a pre-equilibrated High Pressure Liquid Chromatography (HPLC) column and eluted under conditions that separate the nucleotide analogs from the natural nucleotides. Useful media for chromatographic separation of nucleotides, bases, and nucleosides include reverse phase media, such as a reverse phase C18 column or ODS-80T$_M$ or ODS-120T TSK-GEL by Toso-Haas (Montgomeryville, Pa.), anion exchange media, such as DEAE-25SW or SP-25W TSK-GEL by TosoHaas (Montgomeryville, Pa.), or affinity media, such as Boronate-5PW TSK-GEL by TosoHaas (Montgomeryville, Pa.). Example 1 illustrates an embodiment of the present invention using HPLC.

The HPLC column is fitted with an absorbance detector to monitor the column effluent. Hence, "absorbance spectroscopy" for this type of analysis. Typical wavelengths for monitoring HPLC detection of nucleotides are 250 nm, 260 nm and 280 nm. Such separations of nucleotides and nucleotide analogs are well known in the art. Revich et al., *J. Chromatography*, 317:283–300 (1984), and Perrone & Brown, *J. Chromatography*, 317:301–310 (1984) provide examples of the HPLC separation of dNTPs.

Identification of the separated nucleotide analogs can be accomplished by comparison of the retention times (as monitored by absorbance of effluent at various times) of standards of the nucleotide analogs separated on the same HPLC column under the same conditions. Alternatively, the identity of the nucleotide analogs collected in separate fractions after chromatographic separation (as determined by monitoring the absorbance of the column effluent) can be determined by other standard analytical methods, such as nuclear magnetic resonance or atomic analysis (H,C,N).

In this illustrative example using depolymerization with Klenow exo–, the presence of a released identifier nucleotide from a particular probe indicates the presence of the target sequence that hybridizes with that probe.

In an alternative absorbance spectroscopic embodiment, the released nucleotides from a depolymerization reaction mixture are separated on a gas chromatograph fitted with an absorbance detector to monitor column effluent.

In another alternative absorbance spectroscopic detection embodiment, phosphate groups from released nucleotide triphosphates are transferred to ADP using a nucleotide diphosphate kinase (NDPK). The resulting ATP is detected using an absorbance spectroscopic ATP detection system. Several absorbance spectroscopic ATP detection systems are known in the art. An exemplary absorbance spectroscopic ATP detection system is one wherein the ATP acts as a phosphate donor in a glucose-6-phosphate kinase-catalyzed reaction that is observable using absorbance spectroscopic detection.

B. Kits

The invention also contemplates kits for determining the presence or absence of a predetermined nucleic acid target sequence in a nucleic acid sample for analysis by mass spectrometry, fluorescence spectroscopy or absorption spectroscopy. Such kits comprise: (A) a purified and isolated enzyme whose activity is to release one or more nucleotides from the 3' terminus of a hybridized nucleic acid probe; and (B) pyrophosphate.

In some embodiments, a contemplated kit optionally further comprises at least one nucleic acid probe, said nucleic acid probe being complementary to a nucleic acid target sequence and comprising an identifier nucleotide. In some embodiments, the nucleic acid probe includes at least one label, as discussed above. In some embodiments, the nucleic acid probe comprises a nucleotide analogue.

Preferably the enzyme whose activity is to release nucleotides in the kit is a template dependent polymerase that, in the presence of pyrophosphate ions, depolymerizes hybridized nucleic acids whose bases in the 3'-terminal region are matched with total complementarity. In this embodiment, a contemplated kit includes an enzyme capable of catalyzing pyrophosphorolysis. Exemplary enzymes capable of catalyzing pyrophosphorolysis include, but are not limited to Taq polymerase, Tne polymerase, Tne triple mutant polymerase, Tth polymerase, Tvu polymerase, Ath polymerase, T4 DNA polymerase, Klenow fragment, Klenow exo minus, *E. coli* DNA polymerase I, AMV reverse transcriptase, MMLV reverse transcriptase, or poly(A) polymerase. Preferred enzymes capable of catalyzing pyrophosphorolysis are Tne polymerase, Tne triple mutant polymerase, Tth polymerase, Tvu polymerase, Ath polymerase, T4 DNA polymerase, Klenow fragment, and Klenow exo minus, with Tne triple mutant polymerase, Tth polymerase, Tvu polymerase, Ath polymerase particularly preferred; and Tne triple mutant polymerase and Tvu polymerase most particularly preferred.

In an alternative preferred kit, the included enzyme whose activity is to release nucleotides exhibits a 3' to 5' exonuclease activity, is the exonuclease activity of a polymerase. Exemplary polymerases for this embodiment include *E. coli* DNA polymerase I, Klenow or T4 DNA polymerase. Preferred polymerases with 3' to 5' exonuclease activity useful in this embodiment of the invention are Klenow or T4 DNA polymerase.

In an alternative preferred kit, the included enzyme whose activity is to release nucleotides exhibits a 3' to 5' exonuclease activity, depolymerizing hybridized nucleic acids having one or more mismatched bases at the 3' terminus of the hybridized probe. In such an embodiment, the kit contains an exonuclease such as S1 nuclease, nuclease BAL 31, mung bean nuclease and ribonuclease H.

Any of the above enzyme types is utilized in a contemplated method in a depolymerizing effective amount. That is, the enzyme is used in an amount that depolymerizes the hybridized probe to release an identifier nucleotide. This amount can vary with the enzyme used and also with the temperature at which depolymerization is carried out. An enzyme of a kit is typically present in an amount sufficient to permit the use of about 0.1 to 100 U/reaction; in particularly preferred embodiments, the concentration is about 0.5 U/reaction. An amount of enzyme sufficient to carry out at least one assay, with its controls is provided.

Instructions optionally present in such kits instruct the user on how to use the components of the kit to perform the various methods of the present invention. It is contemplated that these instructions include a description of the detection methods of the invention, including detection by mass spectrometry, fluorescence spectroscopy, and absorbance spectroscopy.

The invention contemplates kits optionally containing a nucleic acid probe for a nucleic acid target of interest, said nucleic acid probe being complementary to a predetermined nucleic acid target and comprising an identifier nucleotide. In another embodiment, the kits contain multiple probes, each of which contain a different base at an interrogation position or which are designed to interrogate different target DNA sequences. In a contemplated embodiment, multiple probes are provided for a set of nucleic acid target sequences that give rise to analytical results that are distinguishable for the various probes. Exemplary probes and groups of probes are provided in the parent application, listed above and incorporated herein by reference.

It is contemplated that a kit contain a vessel containing a purified and isolated enzyme whose activity is to release one or more nucleotides from the 3' terminus of a hybridized nucleic acid probe, and a vessel containing pyrophosphate. In one embodiment, these items are combined in a single vessel. It is contemplated that the enzyme is either in solution or provided as a solid (e.g. as a lyophilized powder), the same is true for the pyrophosphate. Preferably, the enzyme is provided in solution. It is further contemplated that a kit contain a vessel containing one or more nucleic acid probes, said nucleic acid probe being complementary to a predetermined nucleic acid target sequence and comprising an identifier nucleotide. Some contemplated kits contain labeled nucleic acid probes. Other contemplated kits further comprise vessels containing labels and vessels containing reagents for attaching the labels.

Yet another embodiment of the invention is a composition for determining the presence or absence of a predetermined nucleic acid target sequence in a nucleic acid sample comprising an aqueous solution that contains: (A) a purified and isolated enzyme whose activity is to release one or more nucleotides from the 3' terminus of a hybridized nucleic acid probe; and (B) pyrophosphate. In some embodiments the composition further comprises one or more nucleic acid probes, said nucleic acid probe(s) being complementary to a predetermined nucleic acid target sequence(s) and comprising an identifier nucleotide.

As discussed above, the nucleic acid probe optionally comprises a label, or a nucleotide analog. The enzymes and probes are as discussed above with respect to the kits. Thus, in some embodiments of a kit or composition, the identifier nucleotide comprises a fluorescent label and the probe optionally further comprises a fluorescence quencher or enhancer. As mentioned above, exemplary useful fluorophores are Fluorescein, 5-carboxyfluorescein (FAM), 2'7' dimethoxy-4'5'-dichloro-6-carbosyfluorescein (JOI), rhodamine, 6-carboxyrhodamine (R6G), N,N,N,N-tetramethyl-6-carboxyrhodamine (TAMRA), 6-carboxy-X-rhodamine (ROX), 4-(4'-dimethylaminophenylazo)benzoic acid (DABCYL), and 5-(2'-aminoethyl)aminonaphthalene-1-sulfonic acid (EDANS). In other embodiments of a kit or composition, the identifier nucleotide comprises a non-natural nucleotide analog.

The following Examples are offered to further illustrate, but not limit the present invention.

EXAMPLE 1

HPLC Separation of dNTPs After Interrogation Assay, But Prior to Phosphate Transfer and Light Production Large-volume pyrophosphorylation assays were performed on matched and mismatched probe/target hybrids. The released nucleotides were separated by high performance liquid chromatography (HPLC) and their fractions collected. NDPK terminal phosphate transfer reactions were performed on these concentrated fractions and luciferase assays conducted to illustrate discrimination between the original matched and mismatched hybrid treated samples.

The oligonucleotides were CV 12 (SEQ ID NO:1), CV 15 (SEQ ID NO:2), and CV 16 (SEQ ID NO:3). CV12 is a target single-stranded DNA that has the nucleotide sequence of a segment of the wild-type genome of cytomegalovirus (CMV). CV15 is a probe oligonucleotide that hybridizes with exact homology to a segment of CV12. CV16 is a probe oligonucleotide that is identical to CV15, except that it contains a one base change from the CV15 sequence at the site of the SNP that confers gancyclovir drug resistance to CMV.

Target/probe hybrids were formed by combining 315 ng of the synthetic wild type CMV target oligonucleotide with either 10.5 $\mu$g wild type CMV probe for a matched hybrid, or 10.5 $\mu$g mutant CMV probe for a mismatched hybrid, and adding water to a final volume of 200 $\mu$L. These solutions were heated to 95° C. for at least 5 minutes, then cooled at room temperature for at least 10 minutes. The following master mix was prepared.

337.5 $\mu$L Nanopure water (Promega, AA399)
90.0 $\mu$L 10×DNA Polymerase buffer (Promega, M195A)
11.25 $\mu$L 40 mM NaPPi (Promega, C113)

Master mix (210 $\mu$L) was added to each of the above hybrid solutions and 5.8 units of Klenow exo− (Promega, M218A) were added to each. The solutions were then incubated at 37° C. for 15 minutes and stored on ice. HPLC separation of the dNTPs was performed.

HPLC separation of dATP, dCTP, dGTP and TTP was performed on a 100×4.6 mm, 3$\mu$ Luna C18 column [Perrone and Brown, *J. Chromatography*, 317:301–310 (1984)] from Phenomenex (Hillerod, Denmark). The column was eluted with a linear gradient of 97 percent buffer A (100 mM triethylammonium acetate, pH 7) to 92 percent buffer A over a period of 12 minutes. The composition of buffer B is 80:20 acetonitrile:35 mM triethylammonium acetate. Detection was monitored by absorbance at 250, 260 and 280 nm. Under these conditions, dCTP was found to elute between 4 and 4.5 minutes, TTP and dGTP eluted as two peaks between 7 and 7.5 minutes, and dATP eluted from 9 to 9.5 minutes.

The fractions containing the free dNTPs were collected and lyophilized. Fraction one contained dCTP, fraction two contained dGTP and TTP, and fraction three contained dATP.

Each fraction was reconstituted in 100 $\mu$L of nanopure water. Ten microliters of each fraction, or 10 $\mu$L of water as a control, were added to a 10 $\mu$L mixture of water, 10×DNA Polymerase Buffer (Promega, M195A), and ADP so that the final concentration was 1×DNA pol buffer and 0.1 $\mu$M ADP. NDPK (0.005 units, Sigma, St. Louis, Mo.) was added to each tube in one set of the tubes and an equal amount of water was added to each tube in the other set of tubes. Samples and controls were incubated at 37° C. for 15 minutes, 10 μL added to 100 μL of L/L reagent and the light output was measured on a Turner® TD10/20 luminometer. The relative light units (rlu) results obtained are shown below:

| Sample | Trial 1 | Trial 2 | Trial 3 | Avg rlu |
|---|---|---|---|---|
| Matched hybrid with NDPK | | | | |
| Fraction 1 | 206.6 | 200.6 | 205.9 | 204.4 |
| Fraction 2 | 839.4 | 851.6 | 833.9 | 841.6 |
| Fraction 3 | 1149.0 | 1150.0 | 1169.0 | 1156 |
| Mismatched hybrid with NDPK | | | | |
| Fraction 1 | 101.8 | 97.0 | 98.9 | 99.9 |
| Fraction 2 | 386.1 | 387.3 | 382.2 | 385.2 |
| Fraction 3 | 412.4 | 409.9 | 416.5 | 412.9 |
| Match hybrid without NDPK | | | | |
| Fraction 1 | 6.8 | 6.5 | — | 6.6 |
| Fraction 2 | 10.9 | 11.5 | — | 11.2 |
| Fraction 3 | 33.0 | 37.8 | — | 35.4 |
| Mismatched hybrid without NDPK | | | | |
| Fraction 1 | 6.2 | 6.7 | — | 6.4 |
| Fraction 2 | 8.3 | 8.4 | — | 8.4 |
| Fraction 3 | 13.4 | 13.5 | — | 13.4 |
| No dNTP | 7.9 | 7.5 | — | 7.7 |

As is seen from the above data, the fraction one match::mismatch ratio is 2.1, fraction 2 match:mismatch ratio is 2.2 and fraction 3 match:mismatch ratio is 2.8. The data therefore demonstrate the utility of using HPLC separation of individual nucleotides followed by NDPK conversion to ATP, the preferred substrate of luciferase. Fraction 3 provides a slightly higher match:mismatch ratio owing to the presence of dATP in the nucleotide HPLC fraction. Nevertheless, HPLC separation of identifier nucleotides is useful in the interrogation assays of the present invention.

```
CV12  5' CCAACAGACGCTCCACGTTCTTTCT-           SEQ ID NO:1
         GACGTATTCGTGCAGCAT

GGTCTGCGAGCATTCCGTGGTAGAAGCGAGCT 3'

CV15  5' CTACCACGAATGCTCGCAGAC 3'              SEQ ID NO:2

CV16  5' CTACCACGAATGCTCGCAGAT 3'              SEQ ID NO:3
```

EXAMPLE 2

Mass Spectrometry for Nucleotide Detection

The mass spectrometer uses the ratio of molecular mass to charge of various molecules to identify them. Nucleic acids are made up of four different base molecules, each with a different mass to charge ratio. In this example, the capability to use mass spectrometry for separation of the nucleotides that make up DNA is demonstrated.

The ESIMS (Electro Spray Ion Mass spectrometry) spectra of 1 μM and 0.1 μM NTP molecules were determined (Fisons Instruments, VG Platform). The samples were prepared by diluting 1:1 with acetonitrile/water/1% $NH_4OH$. A 20 μL injection was made for each sample. Therefore, 10 picomoles of each dNTP are in the 1 μM sample injection, and 1 picomole of each dNTP is in the 0.1 μM sample injection.

Each of the dNTPs is observed in the 1 μM sample along with the dNTP+ Na+peaks. There was a 485 peak also present, which is an impurity in the system or samples. The peaks for each of the dNTPs are significantly diminished in the 0.1 μM sample; only the dATP peak is above the noise level. Therefore, the difference between the 1 and 0.1 μM samples can be qualitatively determined, which indicates the ability to determine the difference between interrogation samples in which the probe and target are matched and mismatched at the 3'-terminal region of the probe.

EXAMPLE 3

Interrogation For Factor V Leiden Mutation: Mass Spectrometry Analysis

This example demonstrates that nucleotides released from the 3'-terminus of a hybridized probe by a process of the invention can be detected by mass spectroscopy. Probes PT5 (SEQ ID NO:4) and PTG (SEQ ID NO:5) are used to PCR-amplify a region of human genomic DNA spanning about 500 base pairs encoding the prothrombin gene. Probe PT5 has phosphorothioate linkages between the first five bases at the 5' end.

The Prothrombin fragment is amplified in a PCR reaction under the following conditions:

| | |
|---|---|
| 5 μL | 10X PCR buffer |
| 5 μL | 25 mM $MgCl_2$ |
| 1 μL | 10 mM dNTPs |
| 1 μL | probe PT5 (50 pmol) |
| 1 μL | probe PT6 (50 pmol) |
| 1 μL | Human genomic DNA (40 ng) |
| 36 μL | water |
| 1.25 U | Taq DNA polymerase |

The PCR cycling parameters are as follows: 94° C., 2 minutes; (94° C., 30 seconds; 60° C., 1 minutes; 70° C., 1 minutes)×40; 70° C., 5 minutes. Fifty units of T7 gene 6 Exonuclease (USB Amersham E70025Y) are added to 25 μL of the PCR reaction and the solution was incubated for 30 minutes at 37° C. Magnetic silica (Promega, A1330) is used to remove free nucleotides from the solution and the remaining DNA is eluted with 100 μL of water.

The prothrombin interrogation probes are 11265 (SEQ ID NO:6), that is totally complementary to a segment of the mutant prothrombin sequence, and 11266 (SEQ ID NO:7), that is totally complementary to a segment of the wild-type prothrombin sequence. Each of these probes has a destabilizing mutation eight bases from the 3'-end.

The purified PCR product is interrogated with each interrogation probe. Two separate interrogation reactions for each of the interrogation probes are assembled as follows.

| 40 µL   | PCR product         |
|---------|---------------------|
| 1.5 nmol | Interrogation oligo |

Water is added to a final volume of 50 µL.

The reactions are incubated at 95° C. for 3 minutes and then at 37° C. for 15 minutes for Klenow exo– reactions. A replicate set of solutions is incubated at 95° C. for 3 minutes and then 55° C. for 15 minutes for the Tne triple mutant reactions.

Fifty microliters of the appropriate master mix are then added. One master mix contains Klenow exo– polymerase and yeast NDPK. The master mix for Klenow exo– is 2 mM sodium pyrophosphate, 0.2 µM ADP, 2×polymerase buffer M195A, 1–2 U Klenow exo– and 0.2 U yeast NDPK. The other master mix contains Tne triple mutant polymerase and Pfu NDPK. The master mix for Tne is 2 mM sodium pyrophosphate, 0.2 µM ADP, 2×polymerase buffer (M1901), 5 mM magnesium chloride, 1 U Tne triple mutant polymerase and 0.1 U Pfu NDPK.

The reaction containing Klenow exo– proceeds at 37° C. for 15 minutes. The reaction containing Tne triple mutant polymerase proceeds at 55° C. for 15 minutes.

The presence or absence of released nucleotides, converted to ATP, is analyzed for by silicon desorption ionization mass spectroscopy (Wei, J. et al., *Nature*, 399:243–246, 1999). This method is sensitive to femtomole and attomole levels of analyte. The samples are prepared as described in that paper. An observance of released nucleotide from either of the reactions containing the mutant probe, 11265, at levels greater than background, indicates the presence of a mutant prothrombin gene in the genomic DNA sample assayed. An observance of released nucleotide from the either reaction containing the wild-type probe, 11266, at levels greater than background, indicates the presence of a wild-type prothrombin gene in the genomic DNA sample assayed.

| PT5   | 5' ATAGCACTGGGAGCATTGAGGC 3' | SEQ ID NO:4 |
| PT6   | 5' GCACAGACGGCTGTTCTCTT 3'   | SEQ ID NO:5 |
| 11265 | 5' GTGATTCTCAGCA 3'          | SEQ ID NO:6 |
| 11266 | 5' GTGATTCTCAGCG 3'          | SEQ ID NO:7 |

EXAMPLE 4

Multiplex Interrogation For Factor V Leiden and Prothrombin Mutation: Mass Spectroscopy Analysis This example demonstrates that nucleotides released from the 3'-terminus of a hybridized probe in a multiplex reaction by a process of the invention can be detected by mass spectroscopy and thereby determine whether a mutant allele exists at one of the loci being studied.

Probes PT5 (SEQ ID NO:4) and PT6 (SEQ ID NO:5) are used to PCR-amplify a region of human genomic DNA spanning about 500 base pairs encoding the prothrombin gene. Probes 10861 (SEQ ID NO:8) and 9828 (SEQ ID NO:9) are used to PCR amplify a region of human genomic DNA spanning about 300 base pairs encoding the Factor V gene. The Factor V and Prothrombin fragments are co-amplified in one PCR reaction under the following conditions:

| 5 µL    | 10X PCR buffer           |
|---------|--------------------------|
| 5 µL    | 25 mM MgCl$_2$           |
| 1 µL    | 10 mM dNTPs              |
| 1 µL    | probe PT5 (50 pmol)      |
| 1 µL    | probe PT6 (50 pmol)      |
| 1 µL    | probe 10861 (50 pmol)    |
| 1 µL    | probe 9828 (50 pmol)     |
| 1 µL    | Human genomic DNA (40 ng) |
| 36 µL   | water                    |
| 1.25 U  | Taq DNA polymerase       |

The PCR cycling parameters are as follows: 94° C., 2 minutes; (94° C., 30 seconds; 60° C., 1 minute; 70° C., 1 minute)×40; 70° C., 5 minutes.

Probe PT5 and 10861 have phosphorothioate linkages between the first five bases at the 5' end. Fifty units of T7 gene 6 Exonuclease (USB Amersham E70025Y) are added to 25 µL of the PCR reaction and the solution is incubated for 30 minutes at 37° C. to digest the unprotected PCR product and other DNA. Magnetic silica (Promega, A1330) is used to remove free nucleotides from the solution and the remaining desired PCR product DNA is eluted with 100 µL of water.

The prothrombin interrogation probe, 11265 (SEQ ID NO:6), is totally complementary to a segment of the mutant prothrombin sequence. The Factor V interrogation probe, 11432 (SEQ ID NO:10), is totally complementary to a segment of the mutant Factor V Leiden mutation sequence. Each of these probes has a destabilizing mutation eight bases from the 3'-end.

The interrogation reactions are assembled with 40 µL of each PCR product and 1.5 nmol of each interrogation probe. Water is added to a final volume of 100 µL. These reactions are assembled in duplicate; one is assayed with Klenow exo– polymerase and yeast NDPK at 37° C., while the other is assayed with Tne triple mutant polymerase and Pfu NDPK at 70° C.

These assembled reactions are incubated at 95° C. for 3 minutes and then at 37° C. for 10 minutes. The assembled reactions may be lyophilized to decrease the volume. The two different master mixes are assembled as described in Example 3. An equal volume of each master mix is separately added to the reaction solutions described above. Then the solution containing Klenow exo– as the polymerase is incubated at 37° C. for 15 minutes, while the solution containing Tne triple mutant polymerase is incubated at between 55° C. and 70° C.

The presence or absence of released nucleotides, converted to ATP, is analyzed for by silicon desorption ionization mass spectroscopy (Wei, J. et al., *Nature*, 399:243–246, 1999). This method is sensitive to femtomole and attomole levels of analyte. The samples are prepared as described in that paper. Essentially, analytes are dissolved in a deionized water/methanol mixture (1:1) at concentrations typically ranging from 0.001 to 10.0 µM. Aliquots (at least 0.5 to 1.0 µL, corresponding to at least 0.5 femtomole to 100 picomole analyte) of solution are deposited onto the porous surfaces and allowed to dry before mass spectrometry analysis. These experiments are performed on a Voyager DE-STR, time-of-flight mass spectrometer (PerSeptive Biosystems) using a pulsed nitrogen laser (Laser Science) operated at 337 nm. Once formed, ions are accelerated into the time-of-flight mass analyzer with a voltage of 20 kV. Other liquid chromatography-mass spectrometry (LC-MS) instrumentation may also be used for analysis (Niessen, W., *J. Chromatog. A*, 794:407–435 (1998)).

An observance of released nucleotide from either of the reactions containing the two mutant probe, at levels greater than background, indicates the presence of a at least one mutant prothrombin or Factor V Leiden allele in the genomic DNA sample assayed.

| 10861 | 5' TGCCCAGTGCTTAACAAGACCA 3' | SEQ ID NO:8 |
| 9828 | 5' TGTTATCACACTGGTGCTAA 3' | SEQ ID NO:9 |
| PT5 | 5' ATAGCACTGGGAGCATTGAGGC 3' | SEQ ID NO:4 |
| PT6 | 5' GCACAGACGGCTGTTCTCTT 3' | SEQ ID NO:5 |
| 11265 | 5' GTGATTCTCAGCA 3' | SEQ ID NO:6 |
| 11432 | 5' GACAAAATACCTGTATTCCTTG 3' | SEQ ID NO:10 |

EXAMPLE 5

Interrogation Using Fluorescence

This example demonstrates that nucleotides released from the 3'-terminus of a probe hybridized to a target nucleic acid of interest by a process of the invention can be detected by mass spectrometry or by fluorimetric HPLC and thereby provide evidence of the presence or absence of the target nucleic acid in a nucleic acid sample or of a specific base at an interrogation position of the target.

The interrogation probe is designed to have a fluorescent label attached to the 3'-terminal nucleotide in a manner such that the label does not interfere with the ability of the depolymerizing enzyme to remove the nucleotide from the probe. Such fluorescent tags, such as fluorescein or rhodamine, are incorporated into the probe during synthesis with the fluorescent molecule attached to the phosphoramadite nucleotide with a linker of at least 6 carbons (Glen Research). Additionally, in this example an identical, but unlabeled, probe is used and released nucleotides are fluorescently labeled only after the nucleotide is released from the probe by a process of the invention.

Probes PT5 (SEQ ID NO:4) and PT6 (SEQ ID NO:5) are used to PCR-amplify a region of human genomic DNA spanning about 500 base pairs encoding the prothrombin gene. Probe PT5 has phosphorothioate linkages between the first five bases at the 5' end. The PCR reaction conditions are detailed in Example 3. The PCR product is treated with T7 gene 6 Exonuclease (USB Amersham) and separated from free nucleotides as described in Example 3.

The prothrombin interrogation probes are 11265 (SEQ ID NO:6), that is totally complementary to a segment of the mutant prothrombin sequence, and 11266 (SEQ ID NO:7), that is totally complementary to a segment of the wild-type prothrombin sequence. Each of these probes has a destabilizing mutation eight bases from the 3' end. Also, each of these probes is synthesized in two forms: with and without a fluorescent nucleotide analog (fluorescein-derivative) at the 3'-terminal nucleotide position. When the probe has the fluorescent tag, it is incorporated during synthesis of the probe as described above.

The purified PCR product is interrogated in separate reactions with each of the four interrogation probes (wild-type and mutant, with and without fluorescent tag). Interrogation reactions for each of the interrogation probes are assembled as follows.

40 μL PCR product
1.5 nmol Interrogation oligo
Water is added to a final volume of 50 μL.

The reactions are incubated at 95° C. for 3 minutes and then at 37° C. for 15 minutes.

Fifty microliters of master mix are then added. The composition of the master mix containing Klenow exo– is described in Example 3 with the exception that there is no ADP and no NDPK. The reaction then proceeds at 37° C. for 15 minutes. The two reactions that do not contain fluorescent-labeled nucleotides are further treated to label the released nucleotides with a fluorescein tag. Jain, R. et al., *Biochem. Biophys. Res. Comm.*, 200:1239–1244 (1994); Shuker, D. et al., *IARC Sci Publ.*, 124:227–232, (1993).

The solutions are then split in half and analyzed using two different methods. In one method, the presence or absence of released nucleotides in the solutions is analyzed by silicon desorption ionization mass spectroscopy. Wei, J. et al., *Nature*, 399:243–246, (1999). This method is sensitive to femtomole and attomole levels of analyte. The samples are prepared for spectrometry as described in that paper. Essentially, analytes are dissolved in a deionized water/methanol mixture (1:1) at concentrations typically ranging from 0.001 to 10.0 μM. Aliquots (at least 0.5 to 1.0 μL, corresponding to at least 0.5 femtomole to 100 picomole analyte) of solution are deposited onto the porous surfaces and allowed to dry before mass spectrometry analysis. These experiments are performed on a Voyager DE-STR, time-of-flight mass spectrometer (PerSeptive Biosystems) using a pulsed nitrogen laser (Laser Science) operated at 337 nm. Once formed, ions are accelerated into the time-of-flight mass analyzer with a voltage of 20 kV. Other liquid chromatography-mass spectrometry (LC-MS) instrumentation may also be used for analysis. Niessen W., *J. Chromatog. A*, 794:407–435 (1998).

In a second method, the presence or absence of released nucleotides in the solutions is analyzed by HPLC using a fluorescence detector as described in Jain, et al. *Biochem Biophys. Res. Comm.*, 200:1239–1244, 1994 or Levitt, B. et al. *Anal Biochem* 137:93–100, 1984.

An observance of released nucleotide from either of the reactions containing the mutant probe, 11265, at levels greater than background (control reactions that contain no enzyme), indicates the presence of at least one mutant prothrombin allele in the genomic DNA sample assayed. An observance of released nucleotide from either reaction containing the wild-type probe, 11266, at levels greater than background, indicates the presence of at least one wild-type prothrombin allele in the genomic DNA sample assayed.

| PT5 | 5' ATAGCACTGGGAGCATTGAGGC 3' | SEQ ID NO:4 |
| PT6 | 5' GCACAGACGGCTGTTCTCTT 3' | SEQ ID NO:5 |
| 11265 | 5' GTGATTCTCAGCA 3' | SEQ ID NO:6 |
| 11266 | 5' GTGATTCTCAGCG 3' | SEQ ID NO:7 |

EXAMPLE 6

Multiplex Interrogation Using Fluorescent Labels

This example demonstrates that nucleotides released from the 3'-terminus of multiple probes, each hybridized to a target nucleic acid of interest, by a process of the invention can be detected by mass spectrometry or by fluorimetric HPLC and thereby provide evidence of the presence or absence of the target nucleic acid in a nucleic acid sample or of a specific base at an interrogation position of the target.

Each interrogation probe is designed to have a different fluorescent label attached to the 3'-terminal nucleotide in a manner such that the label does not interfere with the ability of the depolymerizing enzyme to remove the nucleotide from the probe. Fluorescent tags, such as fluorescein or rhodamine, are incorporated into the probe during synthesis with the fluorescent molecule attached to the phosphoramadite nucleotide with a linker of at least 6 carbons (Glen Research).

Probes PT5 (SEQ ID NO:4) and PT6 (SEQ ID NO:5) are used to PCR-amplify a region of human genomic DNA spanning about 500 base pairs encoding the prothrombin gene. Probes 10861 (SEQ ID NO:8) and 9828 (SEQ ID NO:9) are used to PCR amplify a region of human genomic DNA spanning about 300 base pairs encoding the Factor V gene. These probes and the PCR reaction conditions are detailed in Example 4. The PCR products are treated with T7 gene 6 Exonuclease (USB Amersham) and separated from free nucleotides as described in Example 4.

The prothrombin interrogation probes are 11265 (SEQ ID NO:6), that is totally complementary to a segment of the mutant prothrombin sequence, and 11266 (SEQ ID NO:7), that is totally complementary to a segment of the wild-type prothrombin sequence. Each of these probes has a destabilizing mutation eight bases from the 3'-end. Also, each of these probes is synthesized with a fluorescent nucleotide analog at the 3'-terminal nucleotide position. The prothrombin probes are tagged with fluorescein; the Factor V probes are tagged with rhodamine.

The purified PCR products are interrogated in separate reactions with either both wild-type probes or both mutant probes. Interrogation reactions are assembled as follows:

| 40 µL | each of the two PCR products |
| 1.5 nmol | each of the wild type or each of the mutant labeled interrogation oligos | water is added to a final volume of 100 µL.

The reactions are incubated at 95° C. for 3 minutes and then at 37° C. for 15 minutes. The reactions are then lyophilized to a final volume of 20 µL.

Twenty microliters of master mix are then added. The composition of the master mix containing Klenow exo– is described in Example 3 with the exception that there is no ADP and no NDPK. The reaction then proceeds at 37° C. for 15 minutes.

The solutions are then split in half and analyzed using two different methods. In one method, the presence or absence of released nucleotides in the solutions is analyzed by silicon desorption ionization mass spectroscopy (Wei, J. et al. *Nature*. 399:243–246, 1999). This method is sensitive to femtomole and attomole levels of analyte. The samples are prepared for spectrometry as described in that paper. Essentially, analytes are dissolved in a deionized water/methanol mixture (1:1) at concentrations typically ranging from 0.001 to 10.0 µM. Aliquots (at least 0.5 to 1.0 µL, corresponding to at least 0.5 femtomol to 100 picomol analyte) of solution are deposited onto the porous surfaces and permitted to dry before mass spectrometry analysis.

These studies are performed on a Voyager DE-STR, time-of-flight mass spectrometer (PerSeptive Biosystems) using a pulsed nitrogen laser (Laser Science) operated at 337 nm. Once formed, ions are accelerated into the time-of-flight mass analyser with a voltage of 20 kV. Other liquid chromatography-mass spectrometry (LC-MS) instrumentation may be used for analysis (Niessen W. *J. Chromatogra A* 794:407–435, 1998)

In a second method, the presence or absence of released nucleotides in the solutions is analyzed by HPLC using a fluorescence detector as described in Jain, et al. *Biochem Biophys Res Commun* 200:1239–1244, 1994 or Levitt, B. et al. *Anal Biochem* 137:93–100, 1984.

An observance of released nucleotide from the reactions containing the mutant probes, at levels greater than background (control reactions that contain no enzyme), is indicative of the presence of at least one mutant prothrombin or Factor V Leiden allele in the genomic DNA sample assayed. An observance of released nucleotide from the reaction containing the wild-type probes, at levels greater than background, is indicative of the presence of at least one wild-type prothrombin or Factor V allele in the genomic DNA sample assayed.

| PT5 | 5' ATAGCACTGGGAGCATTGAGGC 3' | SEQ ID NO:4 |
| PT6 | 5' GCACAGACGGCTGTTCTCTT 3' | SEQ ID NO:5 |
| 10861 | 5' TGCCCAGTGCTTAACAAGACCA 3' | SEQ ID NO:8 |
| 9828 | 5' TGTTATCACACTGGTGCTAA 3' | SEQ ID NO:9 |

EXAMPLE 7

Interrogation Using Fluorescence-II

This example demonstrates that nucleotides released from the 3'-terminus of a probe hybridized to a target nucleic acid of interest by a process of the invention are detected by mass spectrometry or by fluorimetric HPLC and thereby provide evidence of the presence or absence of the target nucleic acid in a nucleic acid sample or of a specific base at an interrogation position of the target.

The interrogation probe is designed to have a fluorescent label attached to the 5'-terminal nucleotide. Fluorescent tags, such as fluorescein or rhodamine, are incorporated into the probe during synthesis with the fluorescent molecule attached to the phosphoramadite nucleotide present at the 5'-end of the oligonucleotide that is used as a probe (Glen Research).

Probes PT5 (SEQ ID NO:4) and PT6 (SEQ ID NO:5) are used to PCR-amplify a region of human genomic DNA spanning about 500 base pairs encoding the prothrombin gene. Probe PT5 has phosphorothioate linkages between the first five bases at the 5' end The PCR reaction conditions are detailed in Example 3. The PCR product is treated with T7 gene 6 Exonuclease (USB Amersham) and purified from free nucleotides as described in Example 3.

The prothrombin interrogation probes are 11265 (SEQ ID NO:6), that is totally complementary to a segment of the mutant prothrombin sequence, and 11266 (SEQ ID NO:7), that is totally complementary to a segment of the wild-type prothrombin sequence. Each of these probes has a destabilizing mutation eight bases from the 3' end. And each of these probes has a label at its 5'-end, incorporated during synthesis of the probe as described above.

The purified PCR product is interrogated in separate reactions with each of the two interrogation probes (wild-type and mutant). Interrogation reactions, with the target molecule in molar excess over the probe molecule, for each of the interrogation probes are assembled as follows:

| 40 μLPCR | product |
|---|---|
| 15 pmol | Interrogation oligo | water is added to a final volume of 50 μL.

The reactions are incubated at 95° C. for 3 minutes and then at 37° C. for 15 minutes.

Fifty microliters of master mix are then added. The composition of the master mix containing Klenow exo– is described in Example 3 with the exception that there is no ADP and no NDPK. The reaction then proceeds at 37° C. for 15 minutes. The hybrid is then denatured by incubating the reaction at 95° C. for 3 minutes, adding 100 μL water to dilute the separated strands and placing the resulting denatured solution tube on ice.

The solutions are then split in half and analyzed using two different methods. In one method, the size of the labeled probe in the solutions is analyzed by silicon desorption ionization mass spectroscopy (Wei, J. et al. *Nature*. 399:243–246, 1999). This method is sensitive to femtomole and attomole levels of analyte. The samples are prepared for spectrometry as described in that paper. Essentially, analytes are dissolved in a deionized water/methanol mixture (1:1) at concentrations typically ranging from 0.001 to 10.0 μM. Aliquots (at least 0.5 to 1.0 μL, corresponding to at least 0.5 femtomol to 100 picomol analyte) of solution are deposited onto the porous surfaces and allowed to dry before mass spectrometry analysis.

These studies are performed on a Voyager DE-STR, time-of-flight mass spectrometer (PerSeptive Biosystems) using a pulsed nitrogen laser (Laser Science) operated at 337 nm. Once formed, ions are accelerated into the time-of-flight mass analyzer with a voltage of 20 kV. Other liquid chromatography-mass spectrometry (LC-MS) instrumentation may also be used for analysis (Niessen W. *J. Chromatog. A* 794:407–435 (1998)

In a second method, the size of the denatured labeled probe strand in the solution is analyzed by HPLC using a fluorescence detector as described in Jain, et al. *Biochem. Biophys. Res. Commun.* 200:1239–1244 (1994) or Levitt, B. et al. *Anal. Biochem.* 137:93–100 (1984). The size of the denatured labeled probe strand is confirmed on an ABI 377.

The size of the labeled probe strand present in the denatured solution indicates whether or not a nucleotide was released from the 3'-terminus of the probe, and therefore whether a match or mismatch base pair existed at the 3' terminus of the probe/template hybrid. For the denatured solution containing wild-type probe, the observance of a labeled probe that is shorter than the length of the original probe indicates that there is a matched base at the 3'-terminus of at least one allele in the original sample and therefore, that at least one allele in the original sample is wild-type. For the denatured solution containing mutant probe, the observance of a labeled probe that is shorter than the length of the original probe indicates that there is a matched base at the 3'-terminus of at least one allele in the original sample and therefore, that at least one allele in the original sample is wild-type. In both cases, the analytical output is quantified to determine whether the genotype is homozygous or heterozygous at that locus.

| PT5 | 5' ATAGCACTGGGAGCATTGAGGC 3' | SEQ ID NO:4 |
|---|---|---|
| PT6 | 5'GCACAGACGGCTGTTCTCTT 3' | SEQ ID NO:5 |
| 11265 | 5' GTGATTCTCAGCA 3' | SEQ ID NO:6 |
| 11266 | 5' GTGATTCTCAGCG 3' | SEQ ID NO:7 |

From the foregoing, it will be observed that numerous modifications and variations can be effected without departing from the true spirit and scope of the present invention. It is to be understood that no limitation with respect to the specific examples presented is intended or should be inferred. The disclosure is intended to cover by the appended claims modifications as fall within the scope of the claims.

What is claimed is:

1. A method for determining the presence or absence of a predetermined nucleic acid target sequence in a nucleic acid sample that comprises the steps of:
  (A) providing a treated sample that may contain said predetermined nucleic acid target sequence hybridized with a nucleic acid probe that includes an identifier nucleotide in the 3'-terminal region;
  (B) admixing the treated sample with a depolymerizing amount of an enzyme whose activity is to release one or more nucleotides from the 3'-terminus of a hybridized nucleic acid probe to form a treated reaction mixture, wherein said enzyme catalyzes pyrophosphorolysis;
  (C) maintaining the treated reaction mixture for a time period sufficient to permit the enzyme to depolymerize hybridized nucleic acid and release identifier nucleotide therefrom; and
  (D) analyzing for the presence of released identifier nucleotides to obtain an analytical output obtained by fluorescence spectroscopy, mass spectrometry or absorbance spectroscopy, the analytical output indicating the presence or absence of said nucleic acid target sequence.

2. The method according to claim 1 wherein said analytical output is obtained by fluorescence spectroscopy.

3. The method according to claim 2 wherein said released identifier nucleotide comprises a fluorescent label.

4. The method according to claim 3 wherein said probe further comprises a fluorescence quencher or fluorescence enhancer molecule.

5. The method according to claim 1 wherein said analytical output is obtained by mass spectrometry.

6. The method according to claim 1 wherein said analytical output is obtained by absorbance spectroscopy.

7. The method according to claim 1 wherein said analysis for the presence of released identifier nucleotides is obtained by analyzing the nucleic acid from which identifier nucleotide was released.

8. The method according to claim 1 including the further steps of forming said treated sample by
  (A) admixing a sample to be assayed with one or more nucleic acid probes to form a hybridization composition, wherein the 3'-terminal region of said nucleic acid probes (i) hybridize with partial or total complementarity to said nucleic acid target sequence when that sequence is present in the sample and (ii) include an identifier nucleotide;
  (B) maintaining said hybridization composition for a time period sufficient to form a treated sample that may contain said one predetermined nucleic acid target sequence hybridized with a nucleic acid probe.

9. A method for determining the presence or absence of at least one predetermined nucleic acid target sequence in a nucleic acid sample that comprises the steps of:
  (A) admixing a sample to be assayed with one or more nucleic acid probes to form a hybridization composition, wherein the 3'-terminal region of said nucleic acid probes (i) hybridizes with partial or total complementarity to at least one said predetermined nucleic acid target sequence when that sequence is present in the sample and (ii) includes an identifier nucleotide;
  (B) maintaining said hybridization composition for a time period sufficient to form a treated sample that may contain said predetermined nucleic acid target sequence hybridized with a nucleic acid probe;
  (C) admixing the treated sample with a depolymerizing amount of an enzyme whose activity is to release one or more nucleotides from the 3'-terminus of a hybridized nucleic acid probe to form a treated reaction mixture, wherein said enzyme catalyzes pyrophosphorolysis;
  (D) maintaining the treated reaction mixture for a time period sufficient to permit the enzyme to depolymerize hybridized nucleic acid and release identifier nucleotide therefrom; and
  (E) analyzing for the presence of released identifier nucleotides to obtain an analytical output obtained by fluorescence spectroscopy, mass spectrometry or absorbance spectroscopy, the analytical output indicating the presence or absence of at least one said nucleic acid target sequence.

10. The method according to claim 9 wherein said analytical output is obtained by fluorescence spectroscopy.

11. The method according to claim 10 wherein said released identifier nucleotide includes a fluorescent label.

12. The method according to claim 11 wherein said probe further comprises a fluorescence quencher or fluorescence enhancer molecule.

13. The method according to claim 9 wherein said analytical output is obtained by mass spectrometry.

14. The method according to claim 9 wherein said analytical output is obtained by absorbance spectroscopy.

15. The method according to claim 9 wherein said analysis for the presence of released identifier nucleotides is obtained by analyzing the nucleic acid from which identifier nucleotide was released.

16. A method for determining the presence or absence of a specific base in a nucleic acid target sequence in a sample to be assayed that comprises the steps of:
  (A) admixing a sample to be assayed with one or more nucleic acid probes to form a hybridization composition, wherein the 3'-terminal region of at least one of said nucleic acid probes (i) is substantially complementary to said nucleic acid target sequence and comprises at least one predetermined nucleotide at an interrogation position, and (ii) includes an identifier nucleotide, and wherein said nucleic acid target sequence comprises at least one specific base whose presence or absence is to be determined
  (B) maintaining said hybridization composition for a time period sufficient to form a treated sample, wherein said interrogation position of the probe is a nucleotide that is aligned with said specific base to be identified in said target sequence, when present, so that base pairing can occur;
  (C) admixing the treated sample with an enzyme whose activity is to release one or more nucleotides from the 3'-terminus of a hybridized nucleic acid probe to depolymerize the hybrid and form a treated reaction mixture, wherein said enzyme catalyzes pyrophosphorolysis;

(D) maintaining the treated reaction mixture for a time period sufficient to release an identifier nucleotide therefrom; and (E) analyzing for the presence or absence of released identifier nucleotide to obtain an analytical output by fluorescence spectroscopy, mass spectrometry or absorbance spectroscopy that indicates the presence or absence of said specific base to be identified.

17. The method according to claim 16 wherein the identifier nucleotide is at the interrogation position.

18. The method according to claim 16 wherein said analytical output is obtained by fluorescence spectroscopy.

19. The method according to claim 18 wherein said released identifier nucleotide includes a fluorescent label.

20. The method according to claim 19 wherein said probe further comprises a fluorescence quencher or fluorescence enhancer molecule.

21. The method according to claim 16 wherein said analytical output is obtained by mass spectrometry.

22. The method according to claim 16 wherein said analysis for the presence of released identifier nucleotides is obtained by analyzing the nucleic acid from which identifier nucleotide was released.

23. A method for determining the presence or absence of a first nucleic acid target in a nucleic acid sample containing that target or a substantially identical second target that comprises the steps of:

(A) admixing said sample to be assayed with one or more nucleic acid probes to form a hybridization composition, wherein said first and second nucleic acid targets comprise a region of sequence identity except for at least a single nucleotide at a predetermined position that differs between the targets, and wherein said nucleic acid probe (i) is substantially complementary to said nucleic acid target region of sequence identity and comprises at least one nucleotide at an interrogation position, said interrogation position of the probe being aligned with said predetermined position of a target when a target and probe are hybridized and (ii) includes an identifier nucleotide in the 3'-terminal region;

(B) maintaining said hybridization composition for a time period sufficient to form a treated sample wherein the nucleotide at said interrogation position of said probe is aligned with the nucleotide at said predetermined position of said target in said region of identity;

(C) admixing the treated sample with a depolymerizing amount an enzyme whose activity is to release one or more nucleotides from the 3'-terminus of a hybridized nucleic acid probe to form a treated reaction mixture, wherein said enzyme catalyzes pyrophosphorolysis;

(D) maintaining the treated reaction mixture for a time period sufficient to depolymerize said hybridized nucleic acid probe and release identifier nucleotide therefrom; and (E) analyzing for the presence of released identifier nucleotide to obtain an analytical output obtained by fluorescence spectroscopy, mass spectrometry or absorbance spectroscopy, said analytical output indicating the presence or absence of said nucleotide at said predetermined region and thereby the presence or absence of a first or second nucleic acid target.

24. The method according to claim 23 wherein said analytical output is obtained by fluorescence spectroscopy.

25. The method according to claim 24 wherein said probe further comprises a fluorescence quencher or fluorescence enhancer molecule.

26. The method according to claim 23 wherein said analytical output is obtained by mass spectrometry.

27. The method according to claim 23 wherein said analytical output is obtained by absorbance spectroscopy.

28. The method according to claim 23 wherein said analysis for the presence of released identifier nucleotides is obtained by analyzing the nucleic acid from which identifier nucleotide was released.

29. A method for selectively detecting a poly(A)+ RNA that comprises the steps of:

(A) admixing a sample to be assayed with an oligo(dT) probe to form a hybridization composition, wherein said oligo(dT) probe includes an identifier nucleotide in the 3'-terminal region;

(B) maintaining said hybridization composition for a time period sufficient to form a treated sample wherein said poly(A)+ RNA hybridizes to said oligo(dT) probe;

(C) admixing the treated sample with an enzyme whose activity is to release of one or more nucleotides from the 3'-terminus of a nucleic acid hybrid, including the identifier nucleotide, to form a treated reaction mixture, wherein said enzyme catalyzes pyrophosphorolysis;

(D) maintaining the treated reaction mixture for a time period sufficient to depolymerize hybridized nucleic acid probe and release identifier nucleotides therefrom; and (E) analyzing for the presence of released identifier nucleotide to obtain an analytical output obtained by fluorescence spectroscopy, mass spectrometry or absorbance spectroscopy, said analytical output indicating the presence of said poly(A)+ RNA.

30. The method according to claim 29 wherein said analytical output is obtained by fluorescence spectroscopy.

31. The method according to claim 29 wherein said identifier nucleotide includes a fluorescent label.

32. The method according to claim 31 wherein said probe further comprises a fluorescence quencher or fluorescence enhancer molecule.

33. The method according to claim 31 wherein said analytical output is obtained by mass spectrometry.

34. The method according to claim 29 wherein said analytical output is obtained by mass spectrometry.

35. The method according to claim 29 wherein said analytical output is obtained by absorbance spectroscopy.

36. The method according to claim 29 wherein said analysis for the presence of released identifier nucleotides is obtained by analyzing the nucleic acid from which identifier nucleotide was released.

* * * * *